United States Patent
Shellenberger et al.

(12)

(10) Patent No.: US 11,534,177 B2
(45) Date of Patent: Dec. 27, 2022

(54) FLEXIBLE STABILIZING MEMBER FOR A CLIP APPLIER

(71) Applicant: TELEFLEX MEDICAL INCORPORATED, Morrisville, NC (US)

(72) Inventors: Carson J. Shellenberger, Cary, NC (US); Warren Taylor, Cary, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 397 days.

(21) Appl. No.: 15/927,885

(22) Filed: Mar. 21, 2018

(65) Prior Publication Data

US 2018/0271536 A1 Sep. 27, 2018

Related U.S. Application Data

(60) Provisional application No. 62/474,535, filed on Mar. 21, 2017.

(51) Int. Cl.
*A61B 17/128* (2006.01)
*A61B 17/122* (2006.01)
*A61B 17/00* (2006.01)

(52) U.S. Cl.
CPC ...... *A61B 17/1285* (2013.01); *A61B 17/1222* (2013.01); *A61B 17/1227* (2013.01); *A61B 2017/00477* (2013.01)

(58) Field of Classification Search
CPC ..... A61B 17/10; A61B 17/068; A61B 17/128; A61B 17/122; A61B 17/1227; A61B 17/1285
See application file for complete search history.

(56) References Cited

U.S. PATENT DOCUMENTS

| 929,868 A | 8/1909 | Mueller |
|---|---|---|
| 1,482,290 A | 1/1924 | Elzi |

(Continued)

FOREIGN PATENT DOCUMENTS

| CN | 1846638 A | 10/2006 |
|---|---|---|
| CN | 101543418 A | 9/2009 |

(Continued)

OTHER PUBLICATIONS

International Search Report and Written Opinion issued in PCT/US2018/023648, dated Sep. 4, 2018.

(Continued)

*Primary Examiner* — Diane D Yabut
*Assistant Examiner* — Christina C Lauer
(74) *Attorney, Agent, or Firm* — BakerHostetler

(57) ABSTRACT

A clip applier configured to apply a surgical clip to tissue. The clip applier may include first and second jaw members configured to engage distal portions of the surgical clip. The first and second jaw members may be configured to move relative to each other between an open configuration and a closed configuration. The clip applier may also include a stabilizing member having an end portion secured to the first jaw member. The stabilizing member may be configured to engage a proximal portion of the surgical clip and be compressed from a first configuration when the first and second jaw members are in the open configuration to a second configuration when the first and second jaw members are in the closed configuration. The stabilizing member may have at least one bend that facilitates compression of the stabilizing member.

20 Claims, 15 Drawing Sheets

(56) References Cited

U.S. PATENT DOCUMENTS

| | | |
|---|---|---|
| 1,728,322 A | 9/1929 | Badrian |
| 2,384,697 A | 9/1945 | Riccardi |
| 2,594,102 A | 4/1952 | Vollmer |
| 2,598,901 A | 6/1952 | Garland |
| 2,626,608 A | 1/1953 | Garland |
| 2,635,238 A | 4/1953 | Garland |
| 2,744,251 A | 5/1956 | Vollmer |
| 2,813,269 A | 11/1957 | Jacobs |
| 2,814,222 A | 11/1957 | Sanders |
| 2,881,762 A | 4/1959 | Lowrie |
| 2,890,519 A | 6/1959 | Storz, Jr. |
| 3,032,039 A | 5/1962 | Beaty |
| 3,150,379 A | 9/1964 | Brown |
| 3,172,133 A | 3/1965 | Rizzo |
| 3,446,212 A | 5/1969 | Le Roy |
| 3,463,156 A | 8/1969 | Mcdermott |
| 3,503,396 A | 3/1970 | Pierie |
| 3,503,397 A | 3/1970 | Fogarty |
| 3,503,398 A | 3/1970 | Fogarty |
| 3,766,925 A | 10/1973 | Rubricius |
| 3,825,012 A | 7/1974 | Nicoll |
| 3,827,438 A | 8/1974 | Kees, Jr. |
| 3,867,944 A | 2/1975 | Samuels |
| 3,874,042 A | 4/1975 | Eddleman et al. |
| 3,954,108 A | 5/1976 | Davis |
| 4,120,302 A | 10/1978 | Ziegler |
| 4,274,415 A | 6/1981 | Kanamoto et al. |
| 4,316,468 A | 2/1982 | Klieman et al. |
| 4,325,376 A | 4/1982 | Klieman et al. |
| 4,337,774 A | 7/1982 | Perlin |
| 4,345,600 A | 8/1982 | Rothfuss |
| 4,346,869 A | 8/1982 | MacNeill |
| 4,390,019 A | 6/1983 | Leveen et al. |
| 4,394,864 A | 7/1983 | Sandhaus |
| 4,414,721 A | 11/1983 | Hufnagel |
| 4,418,694 A | 12/1983 | Beroff et al. |
| 4,428,374 A * | 1/1984 | Auburn ............... A61B 17/122 606/120 |
| 4,444,187 A | 4/1984 | Perlin |
| 4,450,840 A | 5/1984 | Mericle et al. |
| 4,458,682 A | 7/1984 | Cerwin |
| 4,471,780 A | 9/1984 | Menges et al. |
| 4,476,865 A | 10/1984 | Failla et al. |
| 4,487,204 A | 12/1984 | Hrouda |
| 4,487,205 A | 12/1984 | Di et al. |
| 4,492,232 A | 1/1985 | Green |
| 4,519,392 A | 5/1985 | Lingua |
| 4,527,562 A | 7/1985 | Mericle |
| 4,534,351 A | 8/1985 | Rothfuss et al. |
| 4,550,729 A | 11/1985 | Cerwin et al. |
| 4,570,633 A | 2/1986 | Golden |
| 4,579,118 A | 4/1986 | Failla |
| 4,588,160 A | 5/1986 | Flynn et al. |
| 4,589,626 A | 5/1986 | Kurtz et al. |
| 4,616,651 A * | 10/1986 | Golden ............... A61B 17/128 606/142 |
| 4,638,804 A | 1/1987 | Jewusiak |
| 4,671,281 A | 6/1987 | Beroff et al. |
| 4,686,983 A | 8/1987 | Leisman et al. |
| 4,712,549 A | 12/1987 | Peters et al. |
| 4,716,886 A | 1/1988 | Schulman et al. |
| 4,726,372 A | 2/1988 | Perlin |
| 4,807,622 A | 2/1989 | Ohkaka et al. |
| 4,822,348 A | 4/1989 | Casey |
| 4,834,090 A | 5/1989 | Moore |
| 4,834,096 A | 5/1989 | Oh et al. |
| 4,854,317 A | 8/1989 | Braun |
| 4,870,965 A | 10/1989 | Jahanger |
| 4,919,152 A | 4/1990 | Ger |
| 4,924,864 A | 5/1990 | Danzig |
| 4,934,364 A | 6/1990 | Green |
| 4,936,447 A | 6/1990 | Peiffer |
| 4,938,764 A | 7/1990 | Glaberson |
| 4,938,765 A | 7/1990 | Rasmusson |
| 4,942,886 A | 7/1990 | Timmons |
| 4,950,275 A | 8/1990 | Donini |
| 4,961,499 A | 10/1990 | Kulp |
| 4,972,949 A | 11/1990 | Peiffer |
| 4,976,722 A | 12/1990 | Failla |
| 5,002,552 A | 3/1991 | Casey |
| 5,009,657 A | 4/1991 | Cotey et al. |
| 5,026,382 A | 6/1991 | Peiffer |
| 5,046,611 A | 9/1991 | Oh |
| 5,047,038 A | 9/1991 | Peters et al. |
| 5,053,045 A | 10/1991 | Schmidt et al. |
| 5,062,846 A | 11/1991 | Oh et al. |
| 5,078,731 A | 1/1992 | Hayhurst |
| 5,100,416 A | 3/1992 | Oh et al. |
| 5,104,395 A | 4/1992 | Thornton et al. |
| 5,112,343 A | 5/1992 | Thornton |
| 5,127,915 A | 7/1992 | Mattson |
| 5,141,514 A | 8/1992 | van Amelsfort |
| 5,160,339 A | 11/1992 | Chen et al. |
| 5,163,945 A | 11/1992 | Ortiz et al. |
| 5,171,251 A | 12/1992 | Bregen et al. |
| 5,171,252 A | 12/1992 | Friedland |
| 5,201,416 A | 4/1993 | Taylor |
| 5,207,692 A | 5/1993 | Kraus et al. |
| 5,234,449 A | 8/1993 | Bruker et al. |
| 5,246,450 A | 9/1993 | Thornton et al. |
| 5,259,405 A | 11/1993 | Hua-Chou |
| 5,279,416 A | 1/1994 | Malec et al. |
| 5,330,442 A | 7/1994 | Green et al. |
| 5,330,487 A | 7/1994 | Thornton et al. |
| 5,366,458 A | 11/1994 | Korthoff et al. |
| 5,405,344 A | 4/1995 | Williamson et al. |
| 5,431,668 A | 7/1995 | Burbank, III et al. |
| 5,462,555 A | 10/1995 | Bolanos et al. |
| 5,464,416 A | 11/1995 | Steckel |
| 5,487,746 A | 1/1996 | Yu et al. |
| 5,501,693 A | 3/1996 | Gravener |
| 5,509,920 A | 4/1996 | Phillips et al. |
| 5,549,621 A | 8/1996 | Bessler et al. |
| 5,569,274 A | 10/1996 | Rapacki et al. |
| 5,575,796 A | 11/1996 | King et al. |
| 5,575,802 A | 11/1996 | McQuilkin et al. |
| 5,591,178 A | 1/1997 | Green et al. |
| 5,607,436 A | 3/1997 | Pratt et al. |
| 5,626,585 A | 5/1997 | Mittelstadt et al. |
| 5,667,516 A | 9/1997 | Allen |
| 5,697,938 A | 12/1997 | Jensen et al. |
| 5,713,911 A | 2/1998 | Racenet et al. |
| 5,713,912 A | 2/1998 | Porter |
| 5,722,982 A | 3/1998 | Ferreira et al. |
| 5,725,542 A | 3/1998 | Yoon |
| 5,797,922 A * | 8/1998 | Hessel ............... A61B 17/122 606/120 |
| 5,810,853 A | 9/1998 | Yoon |
| 5,843,097 A | 12/1998 | Mayenberger et al. |
| 5,846,255 A | 12/1998 | Casey |
| 5,908,430 A | 6/1999 | Appleby |
| 5,921,991 A | 7/1999 | Whitehead et al. |
| 5,925,052 A | 7/1999 | Simmons |
| 5,954,731 A | 9/1999 | Yoon |
| 5,972,003 A | 10/1999 | Rousseau et al. |
| 5,997,548 A | 12/1999 | Jahanger |
| 6,010,516 A | 1/2000 | Hulka |
| 6,013,088 A | 1/2000 | Karavidas |
| 6,015,417 A | 1/2000 | Reynolds, Jr. |
| 6,050,996 A | 4/2000 | Schmaltz et al. |
| 6,131,576 A | 10/2000 | Davis |
| 6,210,419 B1 | 4/2001 | Mayenberger et al. |
| 6,217,590 B1 | 4/2001 | Levinson |
| 6,228,104 B1 | 5/2001 | Fogarty et al. |
| 6,258,105 B1 | 7/2001 | Hart et al. |
| 6,261,303 B1 | 7/2001 | Mayenberger et al. |
| 6,273,887 B1 | 8/2001 | Yamauchi et al. |
| 6,273,902 B1 | 8/2001 | Fogarty et al. |
| 6,277,117 B1 | 8/2001 | Tetzlaff et al. |
| 6,349,727 B1 | 2/2002 | Stewart, Jr. |
| 6,352,541 B1 | 3/2002 | Kienzle et al. |
| 6,387,112 B1 | 5/2002 | Fogarty et al. |
| 6,391,035 B1 | 5/2002 | Appleby et al. |
| 6,419,682 B1 | 7/2002 | Appleby et al. |

(56) References Cited

U.S. PATENT DOCUMENTS

| | | | |
|---|---|---|---|
| 6,537,289 B1 | 3/2003 | Kayan et al. | |
| 6,558,408 B1 | 5/2003 | Fogarty et al. | |
| 6,599,298 B1 | 7/2003 | Forster et al. | |
| 6,695,854 B1 | 2/2004 | Kayan et al. | |
| 6,699,258 B1 | 3/2004 | Sadler et al. | |
| 6,719,766 B1 | 4/2004 | Buelna et al. | |
| 6,780,195 B2 | 8/2004 | Porat | |
| 6,814,742 B2 | 11/2004 | Kimura et al. | |
| 6,824,547 B2 * | 11/2004 | Wilson, Jr. | A61B 17/1285 606/143 |
| 6,837,895 B2 | 1/2005 | Mayenberger | |
| 6,843,253 B2 | 1/2005 | Parkes | |
| 6,863,675 B2 | 3/2005 | Wilson, Jr. | |
| 6,880,699 B2 | 4/2005 | Gallagher | |
| 6,926,712 B2 | 8/2005 | Phan | |
| 6,932,816 B2 | 8/2005 | Phan | |
| 6,989,017 B2 | 1/2006 | Howell et al. | |
| 7,001,412 B2 | 2/2006 | Gallagher et al. | |
| 7,052,504 B2 | 5/2006 | Hughett | |
| 7,094,245 B2 | 8/2006 | Adams et al. | |
| 7,108,699 B2 | 9/2006 | Kobayashi | |
| 7,131,977 B2 | 11/2006 | Fowler | |
| 7,179,265 B2 | 2/2007 | Manetakis et al. | |
| 7,211,091 B2 | 5/2007 | Fowler et al. | |
| 7,211,092 B2 | 5/2007 | Hughett | |
| 7,316,696 B2 | 1/2008 | Wilson, Jr. et al. | |
| 7,326,223 B2 | 2/2008 | Wilson, Jr. | |
| 7,329,266 B2 | 2/2008 | Royse et al. | |
| 7,357,805 B2 | 4/2008 | Masuda et al. | |
| 7,402,164 B2 | 7/2008 | Watson et al. | |
| 7,572,266 B2 | 8/2009 | Young et al. | |
| 7,585,304 B2 | 9/2009 | Hughett | |
| 7,635,374 B2 | 12/2009 | Monassevitch et al. | |
| 7,645,285 B2 | 1/2010 | Cosgrove et al. | |
| 7,648,514 B1 | 1/2010 | Nakao | |
| 7,727,231 B2 | 6/2010 | Swanson | |
| 7,753,908 B2 | 7/2010 | Swanson | |
| 7,785,324 B2 | 8/2010 | Eberl | |
| 7,963,964 B2 | 6/2011 | Santilli et al. | |
| 7,992,757 B2 | 8/2011 | Wheeler et al. | |
| 8,137,368 B2 | 3/2012 | Kayan et al. | |
| 8,262,639 B2 | 9/2012 | Mathias | |
| 8,403,138 B2 | 3/2013 | Weisshaupt et al. | |
| 8,425,412 B2 | 4/2013 | Rucker | |
| 8,465,507 B2 | 6/2013 | Cosgrove et al. | |
| 8,512,357 B2 | 8/2013 | Viola | |
| 8,585,718 B2 | 11/2013 | Disch et al. | |
| 8,764,774 B2 | 7/2014 | Sigmon, Jr. | |
| 8,852,216 B2 | 10/2014 | Cropper et al. | |
| 8,894,666 B2 | 11/2014 | Schulz et al. | |
| 8,900,253 B2 | 12/2014 | Aranyi et al. | |
| 8,945,151 B2 | 2/2015 | Salas | |
| 8,992,566 B2 | 3/2015 | Baldwin | |
| 9,084,596 B2 | 7/2015 | Stanley et al. | |
| 9,119,627 B2 | 9/2015 | Cosgrove et al. | |
| 9,220,507 B1 | 12/2015 | Patel et al. | |
| 9,271,737 B2 | 3/2016 | Castro et al. | |
| 9,282,972 B1 | 3/2016 | Patel et al. | |
| 9,445,820 B2 | 9/2016 | Whiting | |
| 9,456,824 B2 | 10/2016 | Willett et al. | |
| 9,737,309 B1 | 8/2017 | Ad | |
| 9,855,053 B2 | 1/2018 | Bagaoisan et al. | |
| 9,901,352 B2 | 2/2018 | Fago et al. | |
| 9,955,977 B2 | 5/2018 | Martinez et al. | |
| 10,064,623 B2 | 9/2018 | Soutorine et al. | |
| 10,136,898 B2 | 11/2018 | Schmidt et al. | |
| 10,285,712 B2 | 5/2019 | Cosgrove, III et al. | |
| 10,292,712 B2 | 5/2019 | Shankarsetty | |
| 10,307,166 B2 | 6/2019 | Willett et al. | |
| 10,383,637 B2 | 8/2019 | Castro | |
| 10,548,609 B2 | 2/2020 | Ramsey et al. | |
| 10,758,243 B2 | 9/2020 | Salas | |
| 10,925,616 B2 | 2/2021 | Shellenberger et al. | |
| 11,160,559 B2 | 11/2021 | Shellenberger | |
| 11,266,408 B2 | 3/2022 | Shellenberger | |
| 2002/0046961 A1 | 4/2002 | Levinson et al. | |
| 2002/0068946 A1 | 6/2002 | Kortenbach et al. | |
| 2002/0111640 A1 | 8/2002 | Krause et al. | |
| 2002/0169459 A1 | 11/2002 | Porat | |
| 2003/0014060 A1 | 1/2003 | Wilson et al. | |
| 2003/0074009 A1 | 4/2003 | Ramsey et al. | |
| 2003/0158548 A1 | 8/2003 | Phan et al. | |
| 2004/0010272 A1 | 1/2004 | Manetakis et al. | |
| 2004/0040875 A1 | 3/2004 | Gallagher | |
| 2004/0059359 A1 | 3/2004 | Wilson | |
| 2004/0097970 A1 | 5/2004 | Hughett | |
| 2004/0172043 A1 | 9/2004 | Watson et al. | |
| 2005/0090838 A1 | 4/2005 | Sixto, Jr. et al. | |
| 2005/0149063 A1 | 7/2005 | Young et al. | |
| 2005/0149068 A1 | 7/2005 | Williams et al. | |
| 2005/0149069 A1 | 7/2005 | Bertolero et al. | |
| 2005/0165421 A1 | 7/2005 | Wilson, Jr. et al. | |
| 2005/0165422 A1 | 7/2005 | Wilson | |
| 2005/0165423 A1 | 7/2005 | Gallagher et al. | |
| 2005/0165429 A1 | 7/2005 | Douglas et al. | |
| 2005/0171560 A1 | 8/2005 | Hughett | |
| 2005/0234478 A1 | 10/2005 | Wixey et al. | |
| 2005/0240219 A1 | 10/2005 | Kahle et al. | |
| 2005/0277959 A1 | 12/2005 | Cosgrove et al. | |
| 2006/0217749 A1 | 9/2006 | Wilson et al. | |
| 2007/0016228 A1 | 1/2007 | Salas | |
| 2007/0083218 A1 | 4/2007 | Morris | |
| 2007/0118161 A1 | 5/2007 | Kennedy et al. | |
| 2007/0149989 A1 | 6/2007 | Santilli et al. | |
| 2007/0276417 A1 | 11/2007 | Mendes et al. | |
| 2007/0282355 A1 | 12/2007 | Brown et al. | |
| 2008/0287976 A1 | 11/2008 | Weaner et al. | |
| 2008/0312670 A1 | 12/2008 | Lutze et al. | |
| 2009/0012545 A1 | 1/2009 | Williamson et al. | |
| 2009/0088783 A1 | 4/2009 | Kennedy et al. | |
| 2009/0088786 A1 | 4/2009 | Zook et al. | |
| 2009/0112233 A1 | 4/2009 | Xiao | |
| 2009/0171380 A1 | 7/2009 | Whiting | |
| 2009/0240266 A1 | 9/2009 | Dennis | |
| 2010/0057107 A1 | 3/2010 | Sorrentino et al. | |
| 2010/0082047 A1 | 4/2010 | Cosgrove et al. | |
| 2010/0114131 A1 | 5/2010 | Rotunda | |
| 2010/0211080 A1 | 8/2010 | Trivisani et al. | |
| 2010/0274262 A1 | 10/2010 | Schulz et al. | |
| 2010/0274264 A1 | 10/2010 | Schulz et al. | |
| 2010/0274268 A1 | 10/2010 | Singh et al. | |
| 2011/0022079 A1 | 1/2011 | Miles et al. | |
| 2011/0087244 A1 | 4/2011 | Weisshaupt et al. | |
| 2011/0144665 A1 | 6/2011 | Malkowski | |
| 2011/0245848 A1 | 10/2011 | Rosenberg et al. | |
| 2011/0295291 A1 | 12/2011 | Trivisani | |
| 2012/0074200 A1 | 3/2012 | Schmid et al. | |
| 2012/0083803 A1 | 4/2012 | Patel et al. | |
| 2012/0226291 A1 | 9/2012 | Malizia et al. | |
| 2012/0277765 A1 * | 11/2012 | Zammataro | A61B 17/1285 606/142 |
| 2012/0330326 A1 | 12/2012 | Creston et al. | |
| 2013/0006271 A1 | 1/2013 | Vold et al. | |
| 2013/0226200 A1 | 8/2013 | Kappel et al. | |
| 2013/0245651 A1 | 9/2013 | Schmidt et al. | |
| 2013/0245652 A1 | 9/2013 | Cosgrove et al. | |
| 2013/0261642 A1 | 10/2013 | Willeii et al. | |
| 2014/0058411 A1 | 2/2014 | Soutorine et al. | |
| 2014/0207156 A1 | 7/2014 | Malkowski | |
| 2014/0243862 A1 | 8/2014 | Bagaoisan et al. | |
| 2014/0309677 A1 | 10/2014 | Baldwin | |
| 2015/0066057 A1 | 3/2015 | Rockrohr et al. | |
| 2015/0136835 A1 | 5/2015 | Shelton, IV et al. | |
| 2015/0190137 A1 | 7/2015 | Salas | |
| 2015/0320426 A1 | 11/2015 | Cosgrove et al. | |
| 2016/0174981 A1 | 6/2016 | Fago et al. | |
| 2016/0270790 A1 | 9/2016 | Jankowski | |
| 2016/0354089 A1 | 12/2016 | Whiting | |
| 2017/0014135 A1 | 1/2017 | Martin et al. | |
| 2018/0036008 A1 | 2/2018 | Ramsey et al. | |
| 2018/0168659 A1 | 6/2018 | Bagaoisan et al. | |
| 2018/0271527 A1 | 9/2018 | Shellenberger | |
| 2018/0271532 A1 | 9/2018 | Shellenberger | |
| 2018/0271534 A1 | 9/2018 | Shellenberger | |

(56) References Cited

U.S. PATENT DOCUMENTS

| | | |
|---|---|---|
| 2018/0271535 A1 | 9/2018 | Shellenberger et al. |
| 2021/0128159 A1 | 5/2021 | Taylor et al. |
| 2022/0047271 A1 | 2/2022 | Shellenberger |

FOREIGN PATENT DOCUMENTS

| | | |
|---|---|---|
| CN | 103442658 A | 12/2013 |
| CN | 105054989 A | 11/2015 |
| CN | 106037947 A | 10/2016 |
| CN | 106264646 A | 1/2017 |
| EP | 0086640 A2 | 8/1983 |
| EP | 0201344 A2 | 11/1986 |
| EP | 0314064 A2 | 5/1989 |
| EP | 1233705 A2 | 8/2002 |
| EP | 2074954 A1 | 7/2009 |
| EP | 2502578 A1 | 9/2012 |
| EP | 3493747 A1 | 6/2019 |
| EP | 3600084 A1 | 2/2020 |
| GB | 2054027 A | 2/1981 |
| GB | 2069848 A | 9/1981 |
| GB | 2353710 A | 3/2001 |
| GB | 2465560 A | 5/2010 |
| JP | 56-151034 A | 11/1981 |
| JP | 61-007818 B2 | 3/1986 |
| JP | 61-259652 A | 11/1986 |
| JP | 03-178648 A | 8/1991 |
| JP | 5-200039 A | 8/1993 |
| JP | 2002-345828 A | 12/2002 |
| JP | 2004-522468 A | 7/2004 |
| JP | 2004535236 A | 11/2004 |
| JP | 4263594 B2 | 5/2009 |
| JP | 2014-531250 A | 11/2014 |
| JP | 2015-043977 A | 3/2015 |
| WO | 97/38634 A1 | 10/1997 |
| WO | 01/35837 A1 | 5/2001 |
| WO | 01/37742 A2 | 5/2001 |
| WO | 2004/043225 A2 | 5/2004 |
| WO | 2005/107613 A1 | 11/2005 |
| WO | 2006/102578 A1 | 9/2006 |
| WO | 2012/075532 A1 | 6/2012 |
| WO | 2013/040467 A2 | 3/2013 |
| WO | 2016/094647 A1 | 6/2016 |
| WO | 2018/027032 A1 | 2/2018 |
| WO | 2018/175626 A1 | 9/2018 |
| WO | 2020/018784 A1 | 1/2020 |

OTHER PUBLICATIONS

Extended European Search Report received for EP Patent Application No. 18770602, dated Mar. 1, 2021, 12 pages.
International Preliminary Reporton Patentability received for PCT Patent Application No. PCT/US18/023648, dated Oct. 3, 2019, 7 pages.
Office Action received for Japanese Patent Application No. 2019-552017, dated May 24, 2021, 2 pages (English Translation).
Office Action received for Japanese Patent Application No. 2019-552017, dated Nov. 2, 2020, 3 pages (English Translation).
Supplementary Partial European Search Report received for EP Patent Application No. 18770602.3, dated Nov. 18, 2020, 4 pages.

\* cited by examiner

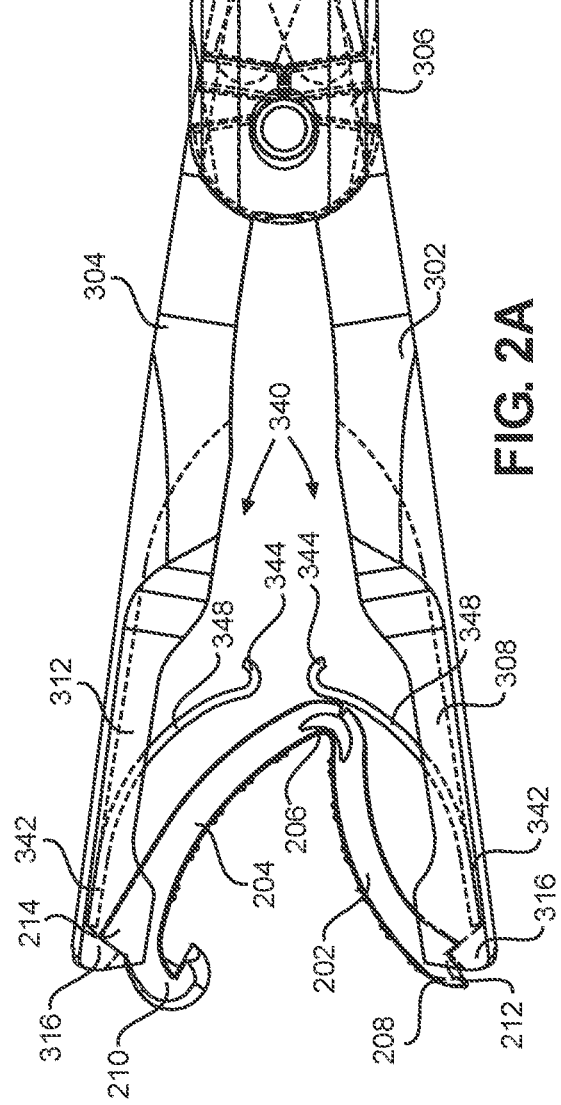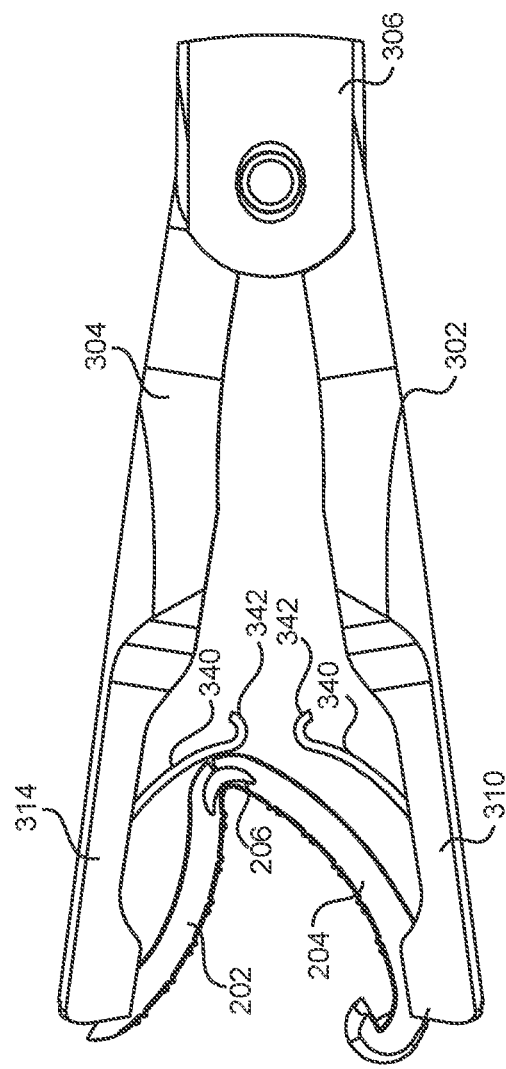

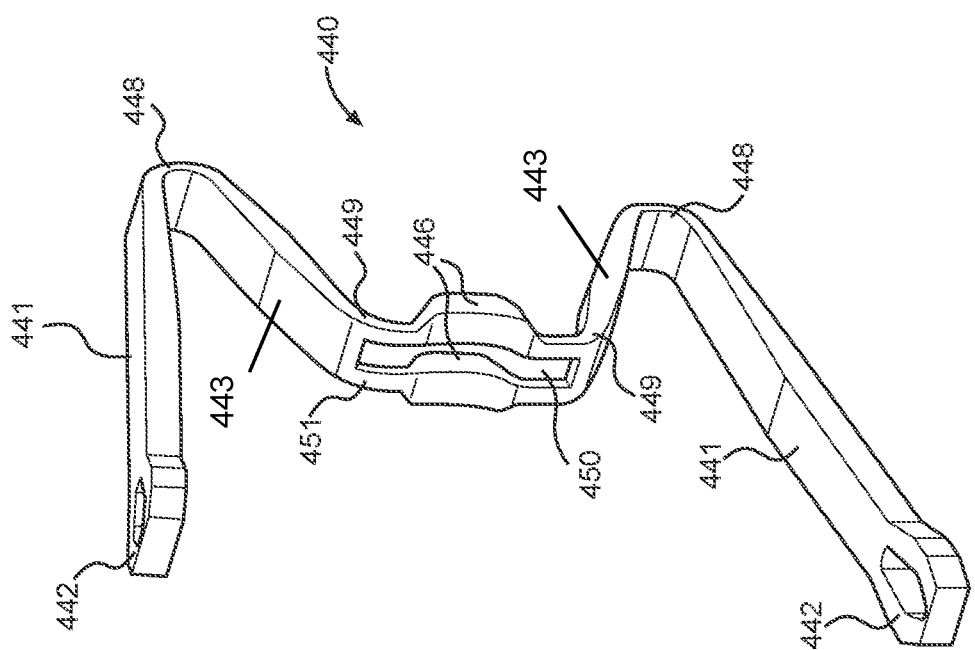

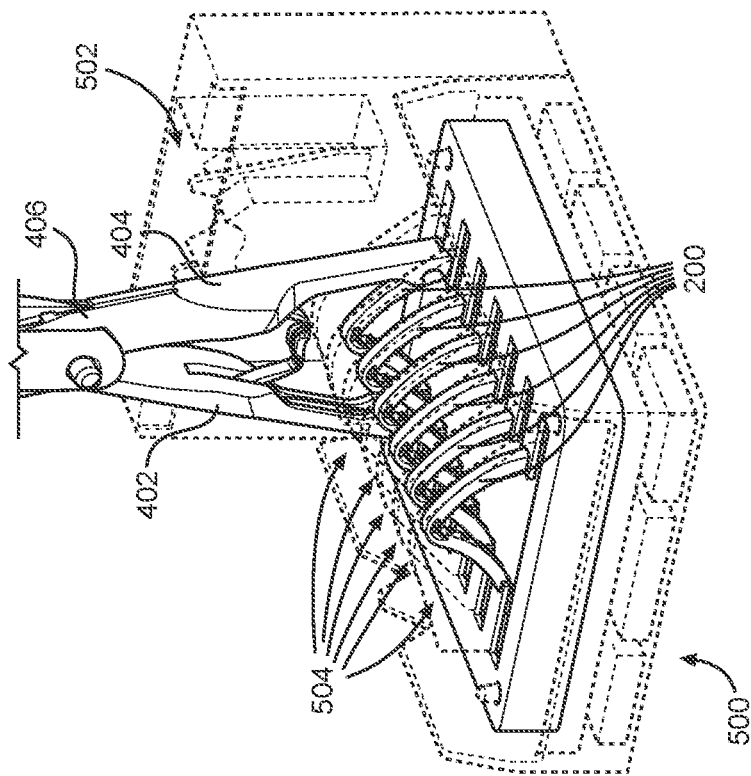
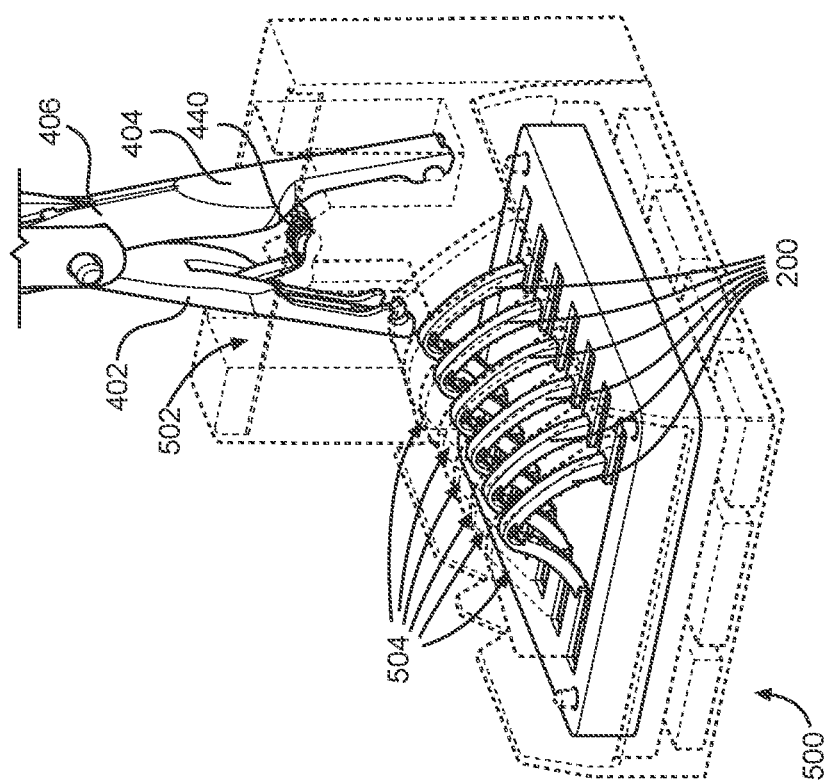

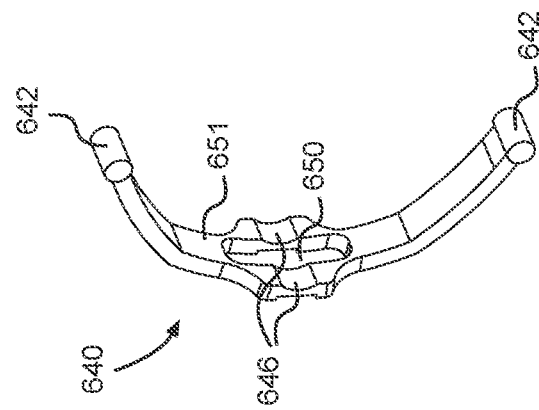
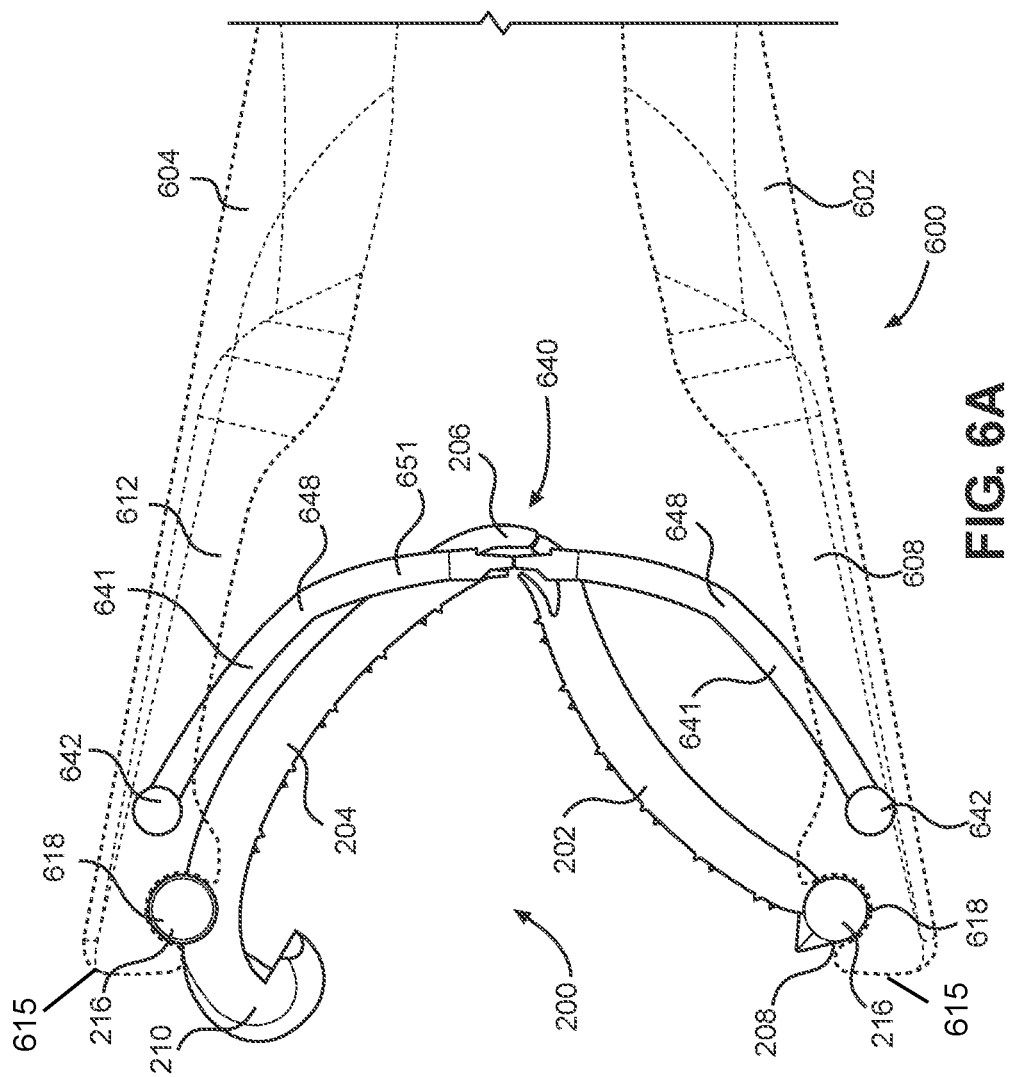

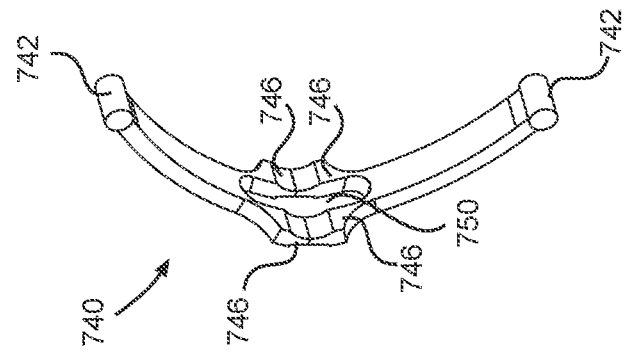
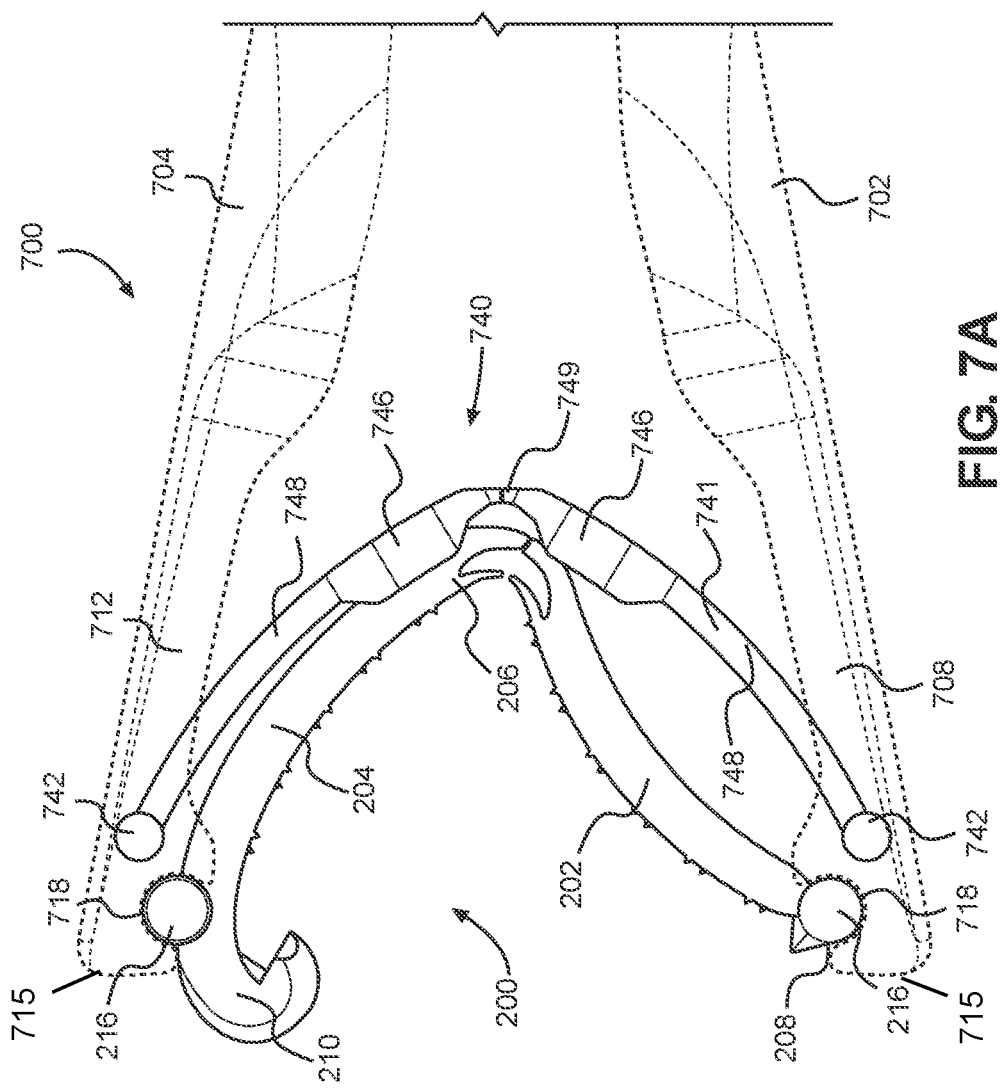
FIG. 7B
FIG. 7A

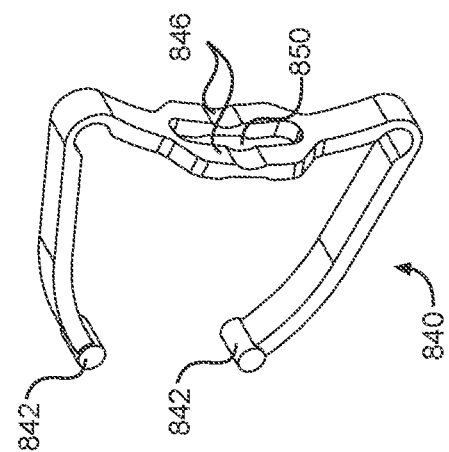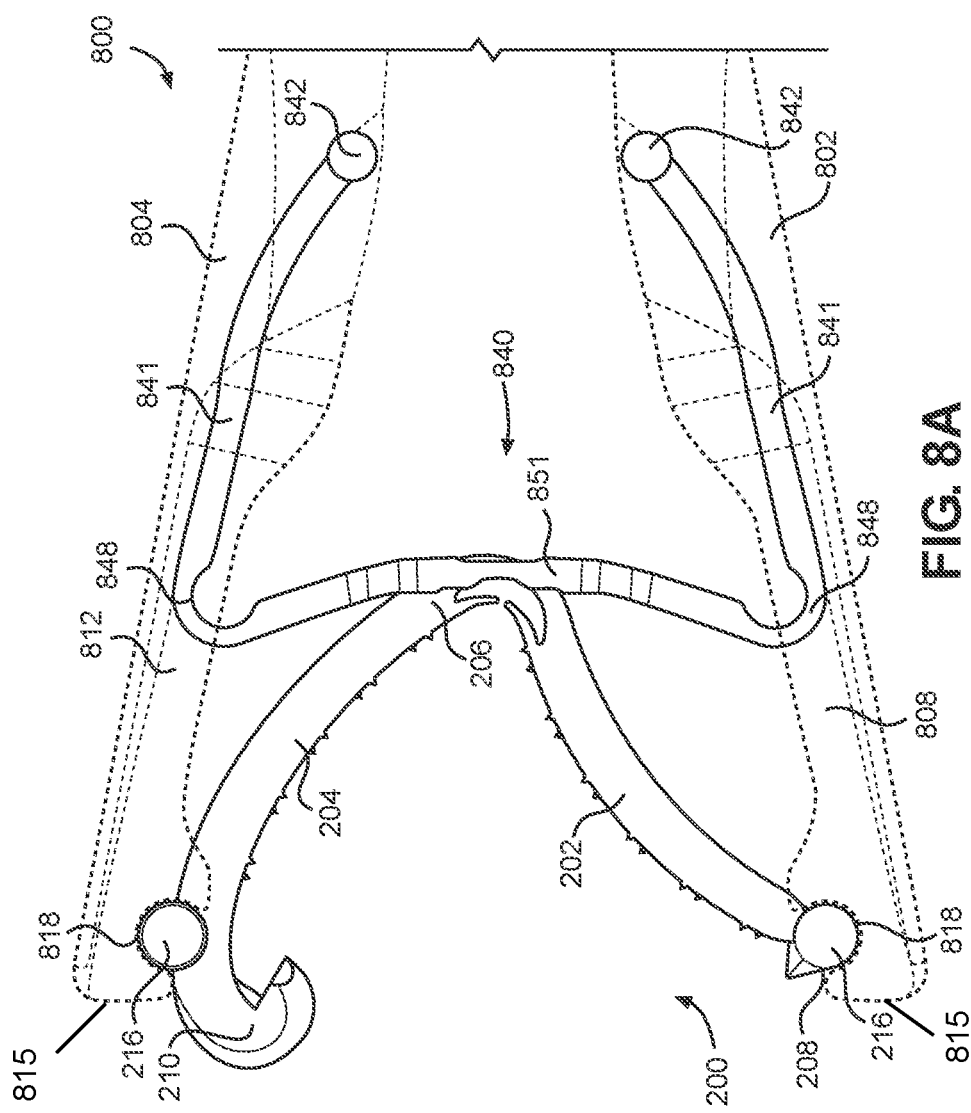

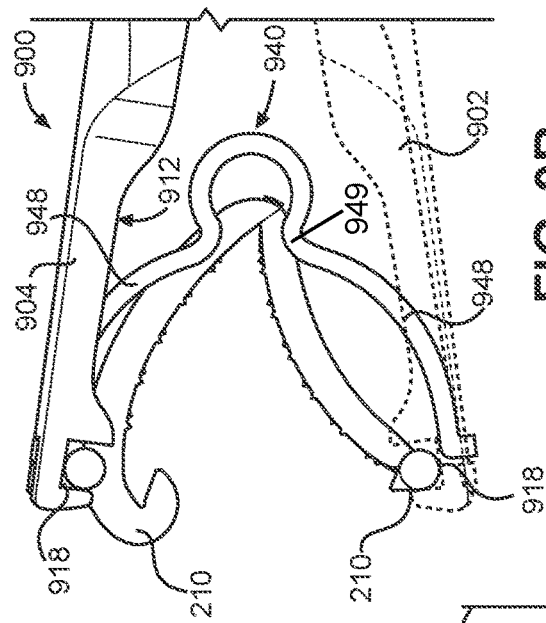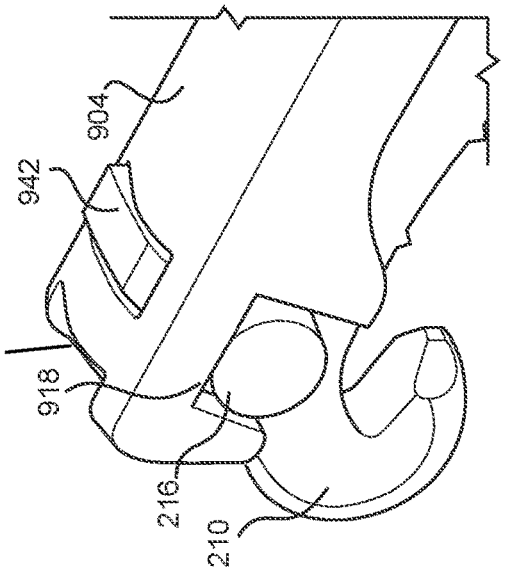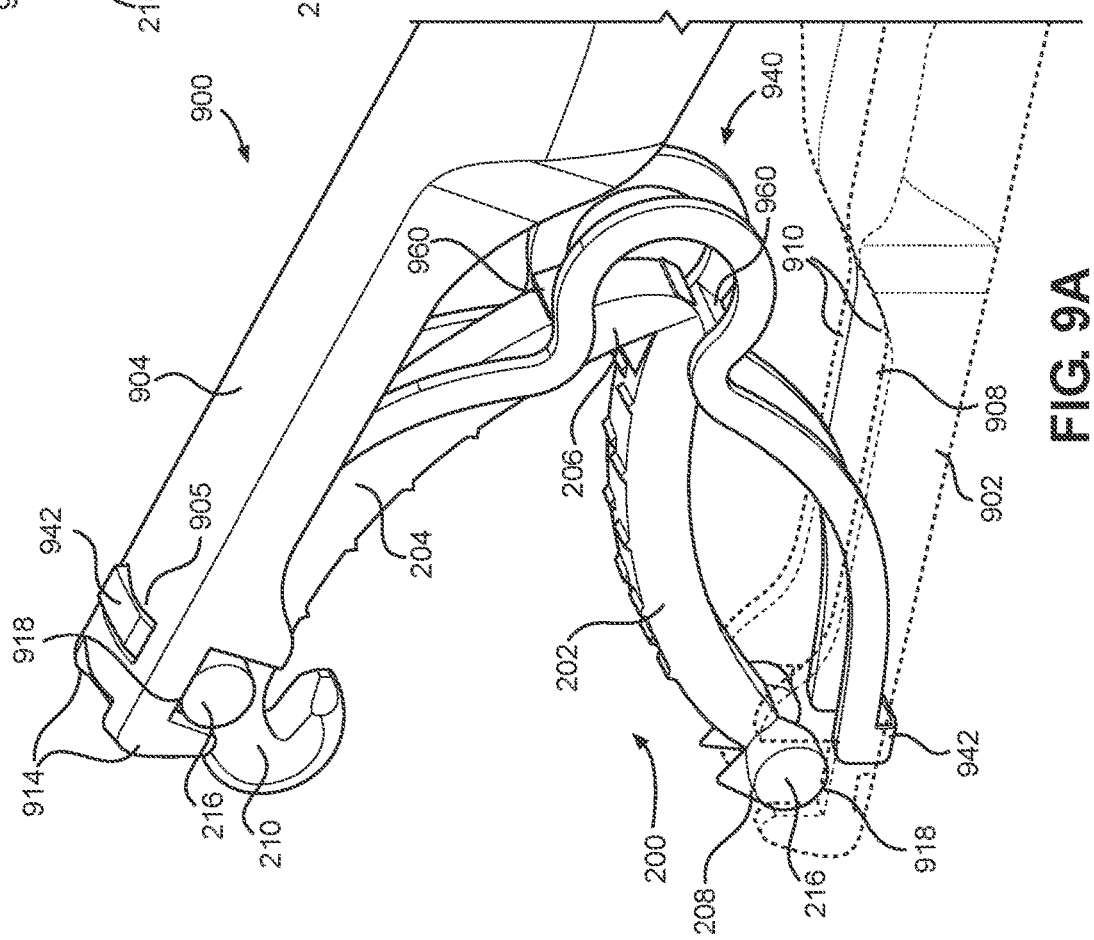

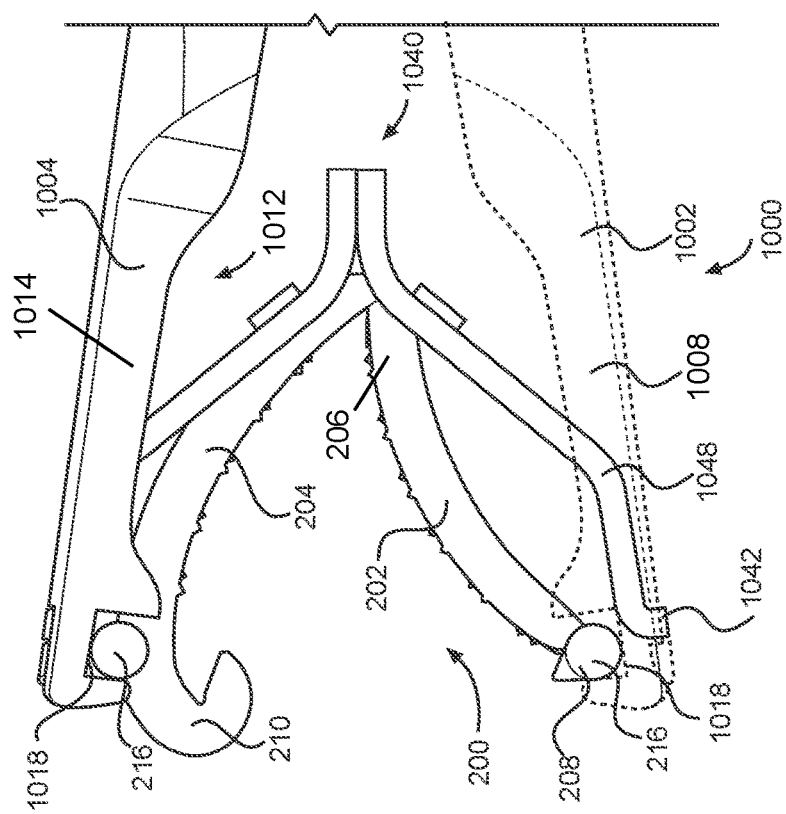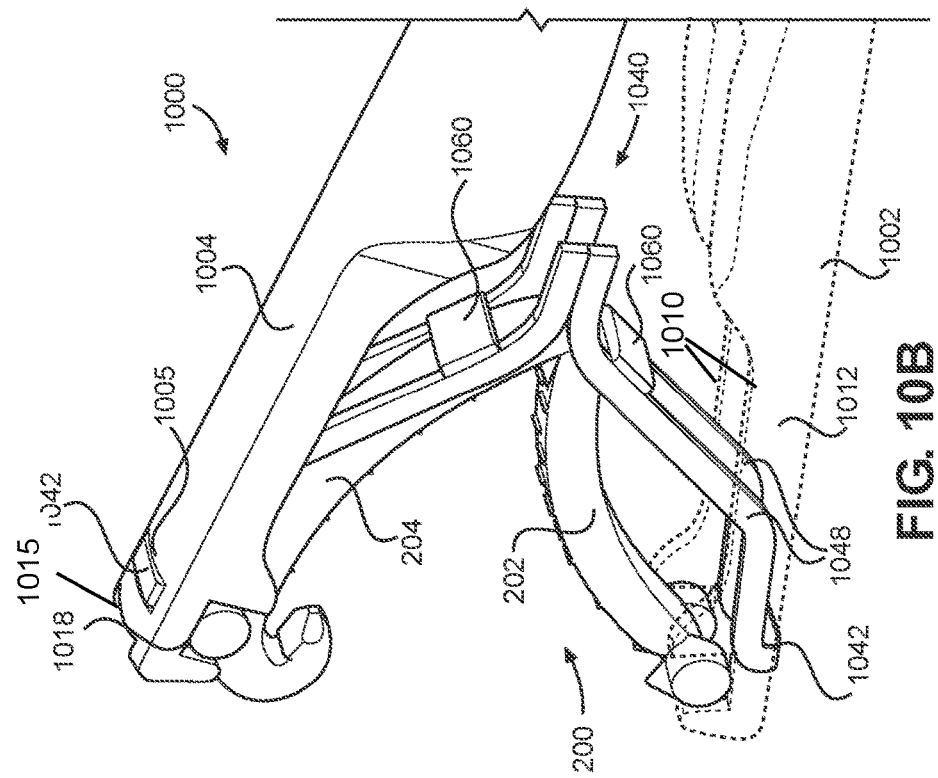

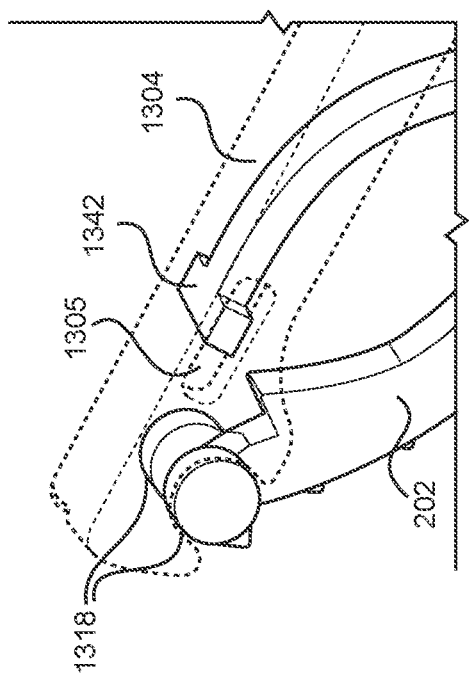
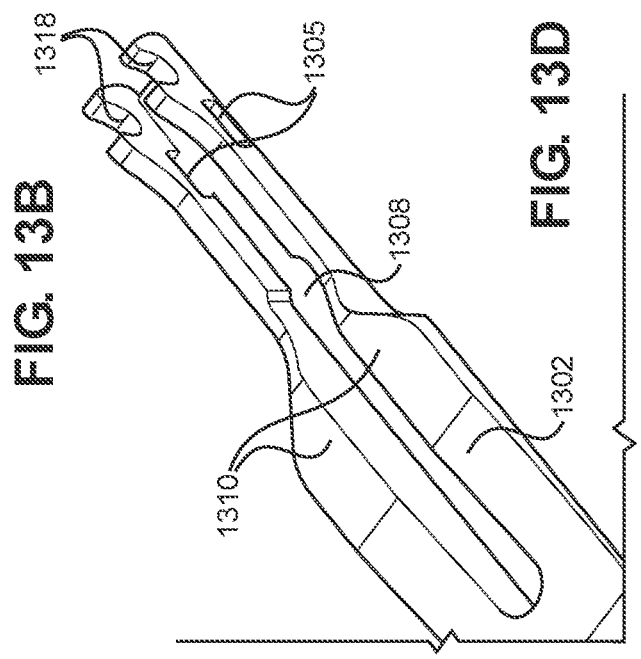
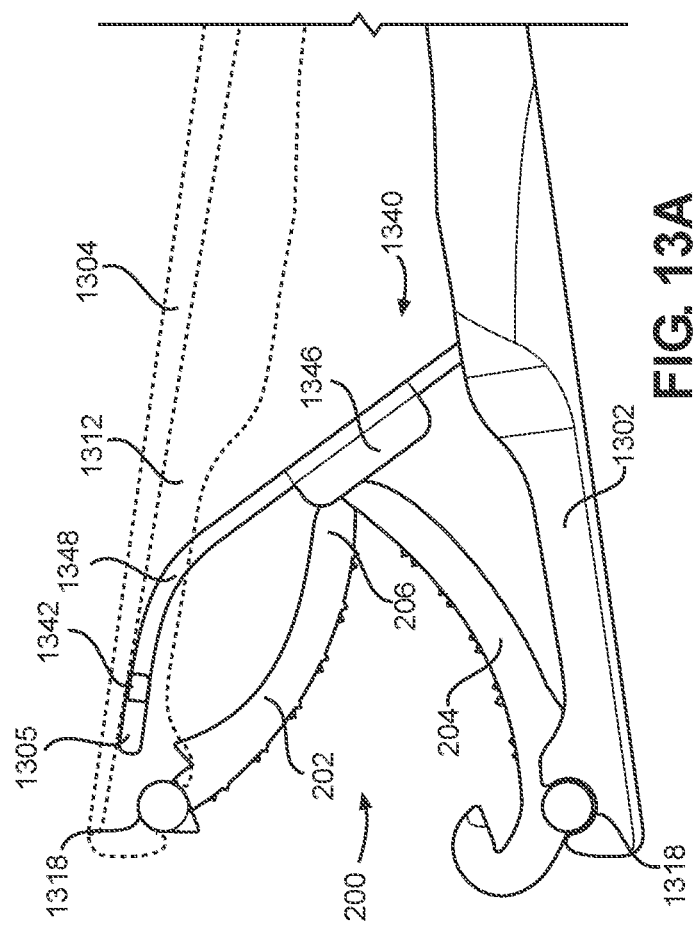
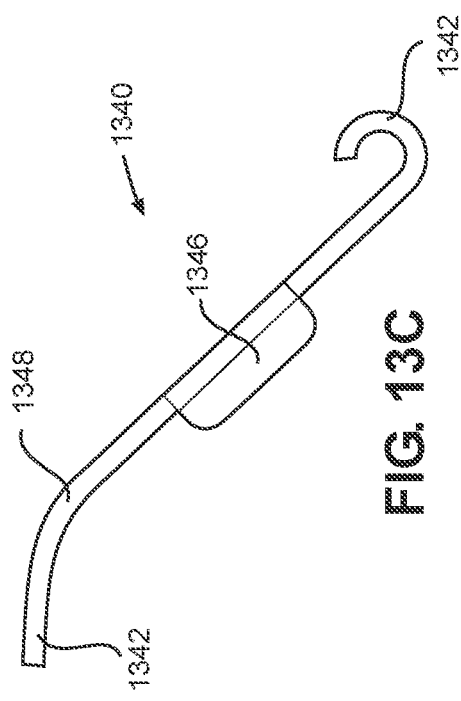

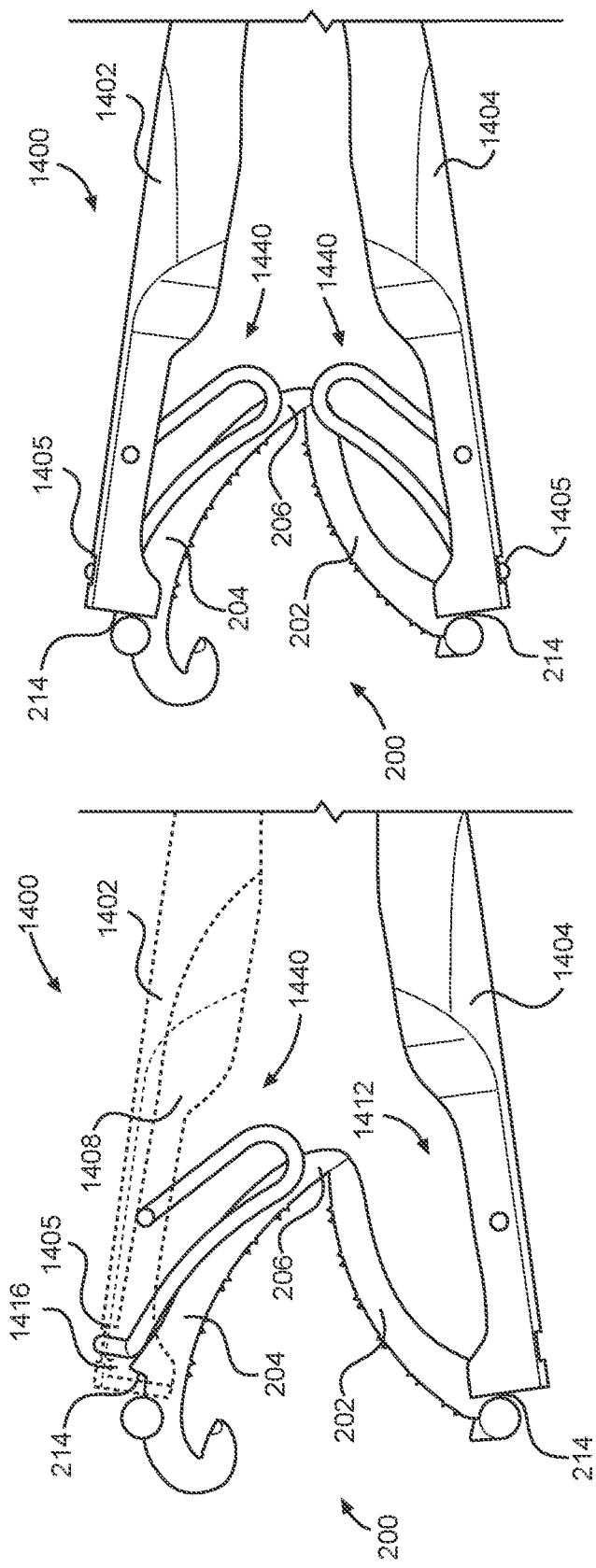

FLEXIBLE STABILIZING MEMBER FOR A CLIP APPLIER

PRIORITY

The present Non-Provisional Patent Application claims priority to U.S. Provisional Patent Application No. 62/474,535, filed on Mar. 21, 2017 and entitled "FLEXIBLE STABILIZING MEMBER FOR A CLIP APPLIER", the entirety of the disclosure of which is incorporated herein.

TECHNICAL FIELD

The present disclosure relates generally to clip appliers, and more particularly, to a flexible stabilizing member for a clip applier.

BACKGROUND

Ligation of tissue (e.g., blood vessels, lymph nodes, nerves, fallopian tubes, and cardiac tissue) is a common practice for many surgical procedures. This can be performed by closing the vessel with a surgical clip or by suturing the vessel with the surgical thread. The use of surgical thread requires complex manipulations of a needle and surgical thread to form knots required to secure the vessel. Such complex manipulations are time consuming and difficult to perform, particularly in endoscopic surgical procedures characterized by limited space and/or visibility. In contrast, surgical clips are relatively quick and easy to apply. Accordingly, the use of surgical clips in endoscopic and open surgical procedures has grown dramatically.

SUMMARY

The present inventors recognize that there is a need to improve one or more features of the clip appliers and/or surgical clips, such as stability of the surgical clip in a clip applier. Surgical clips are often applied by clip appliers with a pair of opposing jaw members. Currently available clip appliers often secure the clip with two points of contact between the opposing jaw members and the leg members of the surgical clip. The two points of contact do not provide sufficient stability to the surgical clip, which can unfavorably move relative to the clip applier during a surgical procedure, or even fall out of the jaw members. The disclosed methods and systems are directed to mitigating or overcoming one or more of the problems set forth above and/or other problems in the prior art.

A first aspect of the present disclosure is directed to a clip applier configured to apply a surgical clip to tissue. The clip applier may include first and second jaw members configured to engage distal portions of the surgical clip. The first and second jaw members may be configured to move relative to each other between an open configuration and a closed configuration. The clip applier may also include a stabilizing member having an end portion secured to the first jaw member. The stabilizing member may be configured to engage a proximal portion of the surgical clip and be compressed from a first configuration when the first and second jaw members are in the open configuration to a second configuration when the first and second jaw members are in the closed configuration.

In some embodiments, the stabilizing member may include first and second walls extending from the stabilizing member and defining a cavity therebetween configured to receive a proximal portion of the surgical clip and to reduce lateral movement of the surgical clip. In some embodiments, the stabilizing member may include an aperture configured to receive a proximal portion of the surgical clip and to reduce lateral movement of the surgical clip. In some embodiment, the stabilizing member may include at least one bend that facilitates compression of the stabilizing member when the first and second jaw members close. In some embodiments, at least one of the first and second jaw members may include a longitudinal channel configured to receive the stabilizing member when compressed. In some embodiments, the stabilizing member may include a second portion secured to the second jaw member. In some embodiments, the clip applier may include a second stabilizing member having an end portion secured to the second jaw member. The second stabilizing member may be configured to be compressed from a first configuration when the first and second jaw members are in the open configuration to a second configuration when the first and second jaw members are in the closed configuration. In some embodiments, the end portion of the stabilizing member may be secured in a longitudinal channel of the first jaw member. In some embodiments, the end portion of the stabilizing member may be releasably secured to the first jaw member. In some embodiments, the end portion of the stabilizing member may include an enlarged end configured to snap into the first jaw member. In some embodiments, the stabilizing member may include a spring element. In some embodiments, the stabilizing member may include a plastic element.

A second aspect of the present disclosure is directed to a stabilizing member configured to be received between first and second jaw members of a clip applier and engage a proximal portion of a surgical clip. The stabilizing member may include a first portion having an enlarged end configured to snap into a first jaw member, and a second portion having an enlarged end configured to snap into a second jaw member. The stabilizing may include at least one bend configured to facilitate compression of the stabilizing member when the first and second jaw members are in a closed configuration, and an aperture between the first and second portions configured to receive a proximal portion of the surgical clip and to reduce lateral movement of the surgical clip.

In some embodiments, the stabilizing member may include first and second walls defining a cavity configured to receive the proximal portion of the surgical clip. In some embodiments, the at least one bend may include a first bend on a first side of the aperture and a second bend on a second side of the aperture. In some embodiments, the stabilizing member may include a spring element. In some embodiments, the stabilizing member may include a plastic element.

A third aspect of the present disclosure is directed to a method of securing a surgical clip to a clip applier having first and second jaw members. The method may include engaging a first end portion of a stabilizing member with the first jaw member, and engaging a second end portion of the stabilizing member with the second jaw member. The method may also include receiving the surgical clip between the first and second jaw members, and securing the surgical clip with the stabilizing member to the clip applier.

In some embodiments, securing the surgical clip with the stabilizing member may include receiving a proximal portion of the surgical clip into an aperture of the stabilizing member. In some embodiments, the method may include: engaging a distal portion of a first leg member of the surgical clip with the first jaw member, and engaging a distal portion of a second leg member of the surgical clip with the second jaw member.

BRIEF DESCRIPTION OF THE DRAWINGS

In order that the disclosure may be readily understood, aspects of this disclosure are illustrated by way of examples in the accompanying drawings.

FIG. 2A illustrates a side view of a first configuration of a second exemplary embodiment of an exemplary clip applier having an exemplary stabilizing member and loaded with an exemplary surgical clip.

FIG. 2B illustrates a side view of a second configuration of the exemplary clip applier having the exemplary stabilizing member and loaded with the exemplary surgical clip of the second exemplary embodiment of FIG. 2A.

FIG. 3C illustrates a perspective view of the exemplary stabilizing member of the third exemplary embodiment of FIGS. 3A-B.

FIG. 5A-B illustrate an exemplary method of loading an exemplary stabilizing member and an exemplary surgical clip into an exemplary clip applier.

FIG. 6A illustrates a side view of a fourth exemplary embodiment of an exemplary clip applier having an exemplary stabilizing member and loaded with an exemplary surgical clip.

FIG. 6B illustrates a perspective view of the exemplary stabilizing member of the fourth exemplary embodiment of FIG. 6A.

FIG. 7A illustrates a side view of a fifth exemplary embodiment of an exemplary clip applier having an exemplary stabilizing member and loaded with an exemplary surgical clip.

FIG. 7B illustrates a perspective view of the exemplary stabilizing member of the fifth exemplary embodiment of FIG. 7A.

FIG. 8A illustrates a side view of a sixth exemplary embodiment of an exemplary clip applier having an exemplary stabilizing member and loaded with an exemplary surgical clip.

FIG. 8B illustrates a perspective view of the exemplary stabilizing member of the sixth exemplary embodiment of FIGS. 8A-C.

FIG. 9A illustrates a perspective view of a seventh exemplary embodiment of an exemplary clip applier having an exemplary stabilizing member and loaded with an exemplary surgical clip.

FIG. 9B illustrates a side view of the exemplary clip applier having the exemplary stabilizing member and loaded with the exemplary surgical clip of the seventh exemplary embodiment exemplary of FIG. 9A.

FIG. 9C illustrates an enlarged view of the exemplary clip applier having the exemplary stabilizing member and loaded with the exemplary surgical clip of the seventh exemplary embodiment of FIGS. 9A-B.

FIG. 10A illustrates a side view of an eighth exemplary embodiment of an exemplary clip applier having an exemplary stabilizing member and loaded with an exemplary surgical clip.

FIG. 10B illustrates a perspective view of the exemplary clip applier having the exemplary stabilizing member and loaded with the exemplary surgical clip of the eighth exemplary embodiment of FIG. 10A.

FIG. 13A illustrates a side view of an eleventh exemplary embodiment of an exemplary clip applier having an exemplary stabilizing member and loaded with an exemplary surgical clip.

FIG. 13B illustrates an enlarged perspective view of the exemplary clip applier with the exemplary stabilizing member and loaded with the exemplary surgical clip of the eleventh exemplary embodiment of FIG. 13A.

FIG. 13C illustrates a side view of the exemplary stabilizing member of the eleventh exemplary embodiment FIGS. 13A-B.

FIG. 13D illustrates an enlarged view of the exemplary clip applier of the eleventh exemplary embodiment of FIGS. 13A-B.

FIG. 14A illustrates a side view of a twelfth exemplary embodiment of an exemplary clip applier having an exemplary stabilizing member and loaded with an exemplary surgical clip.

FIG. 14B illustrates a side view of a thirteenth exemplary embodiment of an exemplary clip applier having an exemplary stabilizing member and loaded with an exemplary surgical clip.

The same or similar reference numbers are used in the drawings and the following detailed description to refer to the same or similar parts.

DETAILED DESCRIPTION

Figure 1A:
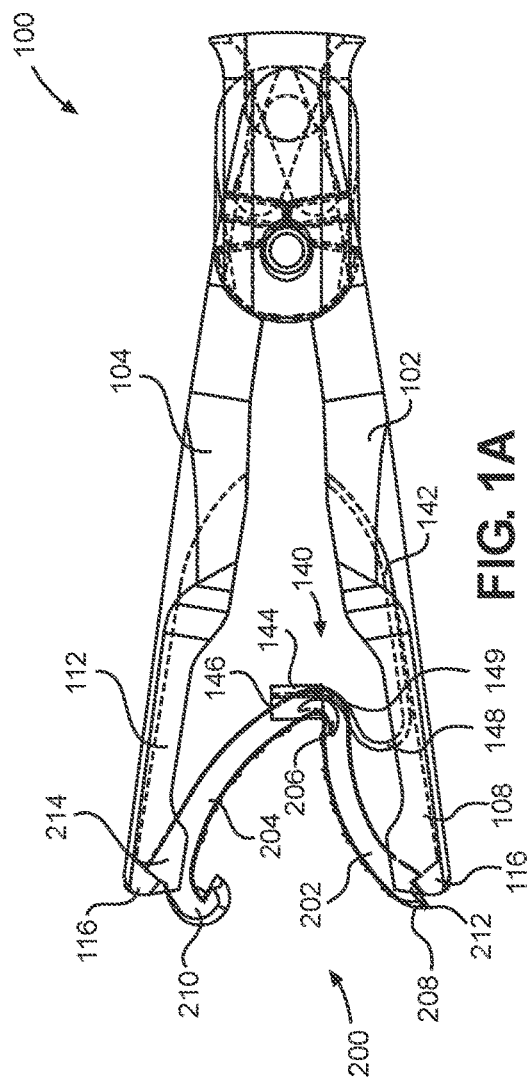
FIG. 1A illustrates a side view of a first exemplary embodiment of an exemplary clip applier having an exemplary stabilizing member and loaded with an exemplary surgical clip.

The invention will now be described with reference to the figures, in which like reference numerals may refer to like parts throughout. In accordance with conventional practice, as used herein, and unless otherwise indicated herein, the term "proximal portion" refers to the specified portion of a device or its component which is generally closer to the medical personnel handling or manipulating the device as it is intended to be used, and the term "distal portion" shall refer to the specified portion of a device or its component which is opposite the proximal portion.

The invention is generally directed to a flexible stabilizing member for a clip applier configured to provide increased stability to a surgical clip disposed between first and second jaw members of the clip applier. The flexibility of the stabilizing member allows for sufficient length to stabilize the surgical clip in an open configuration and for compression during closure of the first and second jaw members of the clip applier. The stabilizing member may also be received or nested in a longitudinal channel in one or both of the jaw members in the closed configuration, such that the stabilizing member does not impede closure of the jaw members. In some embodiments, the stabilizing member may be secured to only one of the first and second jaw members, and in some embodiments, the stabilizing member may be secured to both of the first and second jaw members. In some embodiments, the stabilizing member may be releasably attached to the jaw(s) to facilitate replacement of the component when damaged. In some embodiments, the stabilizing member may be fixed to the jaw(s) to facilitate manufacturing of the clip applier. The stabilizing members may include an aperture configured to receive a proximal portion of the surgical clip. The stabilizing members may be composed of a spring-based metal configured to provide a distal force on the surgical clip to retain the surgical clip in the clip applier, such that bosses may be omitted. The stabilizing member may, alternatively, be composed of a more cost-effective, malleable plastic.

Figure 1B:
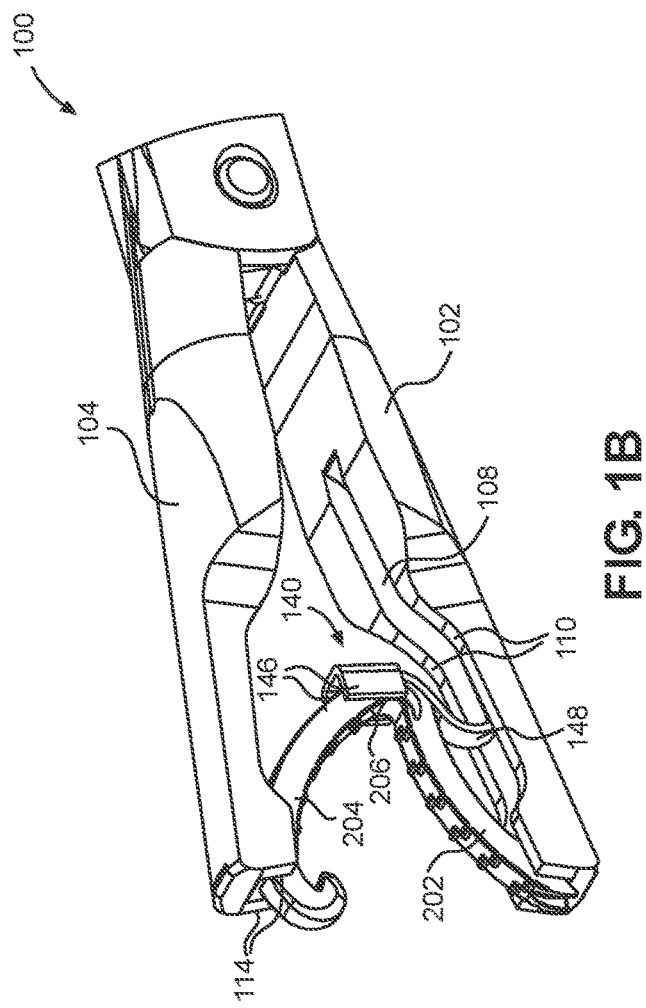
FIG. 1B illustrates a perspective view of the exemplary clip applier having the exemplary stabilizing member and loaded with the exemplary surgical clip of the first exemplary embodiment of FIG. 1A.

FIGS. 1A-B illustrate a clip applier 100 having a stabilizing member 140 and loaded with a surgical clip 200 in an open configuration. As illustrated, the clip applier 100 may have a first jaw member 102 and a second jaw member 104 pivotably coupled at a hinge member 106. The first and second jaw members 102, 104 may be configured to compress the surgical clip 200 onto tissue, for example, to ligate a blood vessel.

The surgical clip 200 may have a first leg member 202 and a second leg member 204 pivotably joined at a hinge member 206. The first leg member 202 may have a generally convex inner surface, a generally concave outer surface, and a tip member 208 on a distal portion. The second leg member 204 may have a generally concave inner surface, a generally convex outer surface, and a hook member 210 on a distal portion. The hook member 210 may engage and deflect around the tip member 208, while one or both of the first and second leg members 202, 204 pivot, straighten, and/or lengthen. The tip member 208 may then be received in the hook member 210 to secure the surgical clip 200 in a latched configuration, as further described in U.S. Pat. No. 4,834,096, the disclosure of which is expressly incorporated herein in its entirety. Each of the first and second leg members 202, 204, may have one or more engagement members 212, 214 on a distal portion. The engagement members 212, 214 may include one or more angled surfaces formed by the leg members 202, 204. As further illustrated in FIG. 1A-B, the engagement member 212 of the first leg member 202 may include a distally facing notch at the tip member 208, forming a pair of angled surfaces, and the engagement member 214 of the second leg member 204 may include a distally facing angled surface on an outer surface, proximal of the hook member 210.

As further illustrated, the first and second jaw members 102, 104 may include at least one engagement member 116 at a distal portion and the stabilizing member 140 proximal of the at least one engagement member 116. A first longitudinal channel 108 may extend through an inner portion of the first jaw member 102, separating the first jaw member 102 into a pair of first extensions 110. A second longitudinal channel 112 may extend through an inner portion of the second jaw member 104, separating the second jaw member 104 into a pair of second extensions 114. The at least one engagement member 116 may be disposed inside of the first and second channels 108, 112 and include an angled surface configured to engage the angled surfaces of the engagement member 212, 214 of the surgical clip 200. For example, the engagement member 116 of the first jaw member 102 may be received in the notch of the first leg member 202, and the engagement member 116 of the second jaw member 104 may abut the distal facing surface of the second leg member 204.

The stabilizing member 140 may have a first end portion 142 fixedly secured to the first jaw member 102 inside of the first channel 108 through a weld or an adhesive), and a second end portion 144 configured to engage the proximal portion of the surgical clip 200. The stabilizing member 140 may be a spring element (e.g., spring steel) configured to provide a distal force on the surgical clip 200, urging the engagement members 212, 214 into engagement with the engagement members 116 of the clip applier 100. In this manner, the surgical clip 200 may be secured in the clip applier, without bosses on the surgical clip 200. The stabilizing member 140 may also include first and second longitudinal walls 146 on opposing sides of the second portion portion 144. The longitudinal walls 146 may define a cavity therein that receives the proximal portion (e.g., the hinge member 206) of the surgical clip 200 and aligns the surgical clip 200 by reducing lateral movement of the proximal portion. The stabilizing member 140 may compress and/or pivot proximally as the first and second jaw members 102, 104 close the surgical clip 200. For example, pivoting, straightening, and/or lengthening of the first and second leg members 202, 204 may apply a proximal force on the stabilizing member 140 to compress and/or pivot the stabilizing member 140 proximally. The stabilizing member 140 may further compress and/or pivot proximally as the stabilizing member 140 is engaged by the second jaw member 104. The stabilizing member 140 may be received into the first and/or second channels 108, 112 as the first and second jaw members 102, 104 approximate and/or close. The compressing and/or pivoting of the stabilizing member 140 may allow the surgical clip 200 to lengthen as it closes and prevent the stabilizing member 140 from impeding the closure of the first and second jaw members 102, 104. The compressing and/or pivoting of the stabilizing member 140 may be facilitated by at least one bend 148 of about 180 degrees, as illustrated in FIGS. 1A-B. The stabilizing member 140 may further include an additional bend 149 proximate to the second end portion 144 to form a seat for the proximal portion of the surgical clip 200, providing additional vertical stability.

FIGS. 2A-B illustrate a clip applier 300 having first and second stabilizing members 340 and loaded with a surgical clip 200 in an open configuration. As illustrated, the clip applier 300 may have a first jaw member 302 and a second jaw member 304 pivotably coupled at a hinge member 306. The first and second jaw members 302, 304 may be configured to compress the surgical clip 200 onto tissue, for example, to ligate a blood vessel.

As further illustrated, the first and second jaw members 302, 304 may include at least one engagement member 316 at a distal portion and the first and second stabilizing members 340 proximal of the at least engagement member 316. A first longitudinal channel 308 may extend through an inner portion of the first jaw member 302, separating the first jaw member 302 into a pair of first extensions 310. A second longitudinal channel 312 may extend through an inner portion of the second jaw member 304, separating the second jaw member 304 into a pair of second extensions 314. The at least one engagement member 316 may be positioned inside of the first and second channels 308, 312 and include an angled surface configured to engage the angled surfaces of the engagement member 212, 214 of the surgical clip 200. For example, the engagement member 316 of the first jaw member 302 may be received in the notch of the first leg member 202, and the engagement member 316 of the second jaw member 304 may abut the distal facing surface of the second leg member 204.

Each of the stabilizing members 340 may have a first end portion 342 fixedly secured to one of the first and second jaw members 302 inside of the respective longitudinal channel 308, 312 (e.g., through a weld or an adhesive), and a second end portion 344 configured to engage the proximal portion the hinge member 206) of the surgical clip 200. The stabilizing members 340 may be a spring element (e.g., spring steel) configured to provide a distal force on the surgical clip 200, urging the engagement members 212, 214 into engagement with the engagement members 316 of the clip applier 300. In this manner, the surgical clip 200 may be secured in the clip applier 300, without bosses on the surgical clip 200. The stabilizing members 340 may compress and/or pivot proximally as the first and second jaw members 302, 304 close the surgical clip 200. Pivoting, straightening, and/or lengthening of the first and second leg members 302, 304 may provide a proximal force to the stabilizing members 340 to compress and or pivot the stabilizing member 340 proximally. The stabilizing members 340 may further compress and/or pivot proximally as the stabilizing members 340 are engaged by the opposing jaw member 302, 304 and/or stabilizing member 340. The stabilizing members 340 may be received into the first and/or second longitudinal channels 308, 312 as the first and second jaw members 302, 304 approximate and/or close. The compressing and/or pivoting of the stabilizing members 340 may allow the surgical clip 200 to lengthen as it closes and prevent the stabilizing members 340 from impeding the closure of the first and second jaw members 302, 304. The compressing and/or pivoting of the stabilizing members 340 may also be facilitated by at least one bend 348 extending along substantially the entire length of the stabilizing member 340. The second end portion 344 may further include a rounded portion to increase contact surface between the stabilizing members 340 when the first and second jaw members 302, 304 are compressed. As further illustrated in FIGS. 2A-B, the stabilizing members 340 may be symmetric, and the jaw members 302, 304 may receive the surgical clip in either orientation.

Figure 3B:
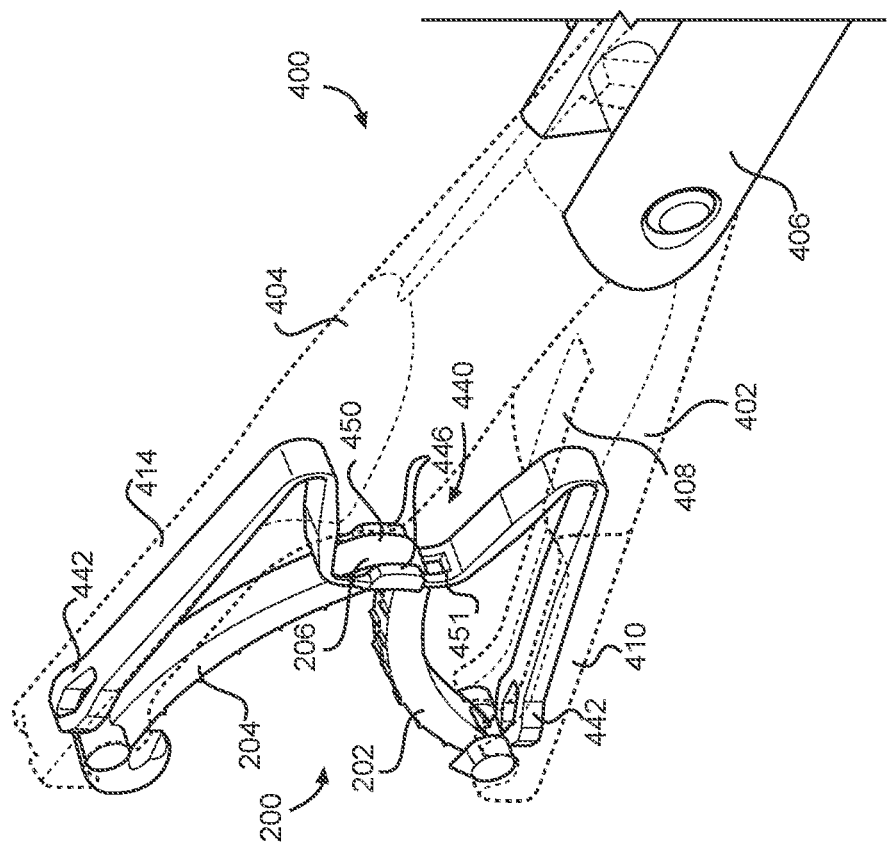
FIG. 3B illustrates a perspective view of the exemplary clip applier having the exemplary stabilizing member and loaded with the exemplary surgical clip of the third exemplary embodiment of FIG. 3A.
Figure 3A:
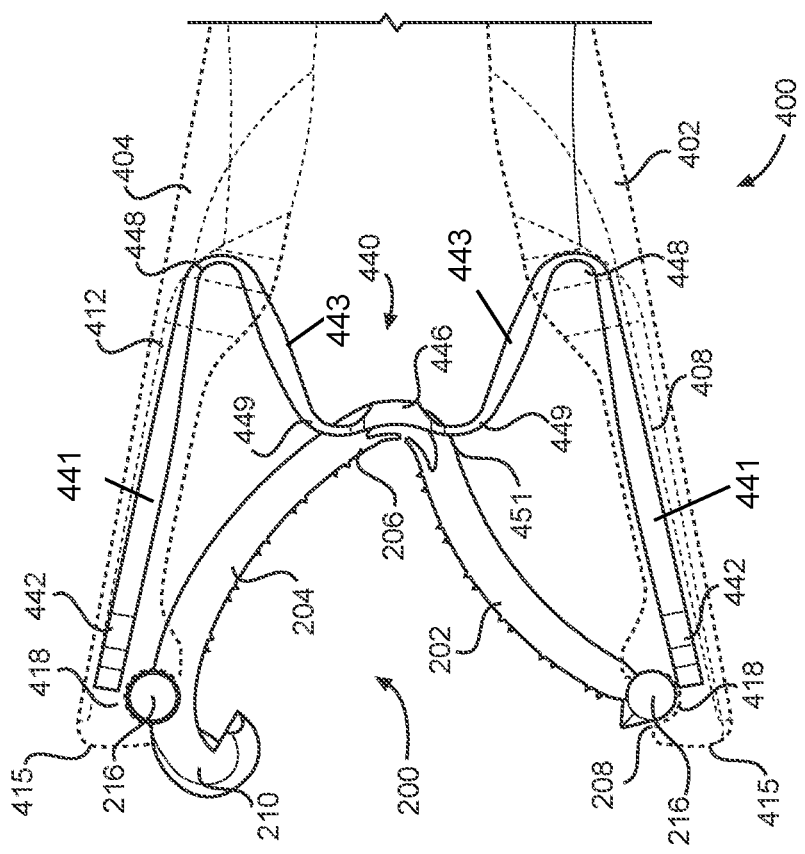
FIG. 3A illustrates a side view of a third exemplary embodiment of an exemplary clip applier having an exemplary stabilizing member and loaded with an exemplary surgical clip.

FIGS. 3A-B illustrate a clip applier 400 having a stabilizing member 440 and loaded with a surgical clip 200 in an open configuration, and FIG. 3C illustrates the stabilizing member 440. As illustrated, the clip applier 400 may have a first jaw member 402 and a second jaw member 404 pivotably coupled at a hinge member 406. The first and second jaw members 402, 404 may be configured to compress the surgical clip 200 onto tissue, for example, to ligate a blood vessel.

As further illustrated, the first and second jaw members 402, 404 may include at least one recess 418 at a distal portion and the stabilizing member 440 proximal of the at least one recess 418. A first longitudinal channel 408 may extend through an inner portion of the first jaw member 402, separating the first jaw member 402 into a pair of first extensions 410. A second longitudinal channel 412 may extend through an inner portion of the second jaw member 404, separating the second jaw member 404 into a pair of second extensions 414. Each of the extensions 410, 414 may have a recess 418 configured to receive opposing boss members 216, and each of the longitudinal channels 408, 412 may be configured to receive a portion of the surgical clip 200. Each of the first and second jaw members 402, 404 may have an open distal end 415 into the longitudinal channels 408, 412 to receive the stabilizing member 440.

The stabilizing member 440 may have leg members 441 with end portions 442 releasably securable to the first and second jaw members 402 inside of the respective longitudinal channel 408, 412. As illustrated in FIG. 3C, the end portions 442 may be enlarged having a split-let configuration with segments spaced apart by an aperture and biased away from each other. The segments of the end portions 442 may be configured to collapse as the end portions 442 are received in the open distal ends 415, and the segments of the end portions 442 may expand to frictionally engage the longitudinal channel 408, 412 to releasably secure the stabilizing member 440 in the first and second jaw members 402, 404. In this configuration, the stabilizing member 440 may abut a proximal wall of the longitudinal channel 408, 412. After use, the stabilizing member 440 may be removed, for example, by pulling the stabilizing member 440 distally out of the first and second jaw members 402, 404. However, it is also contemplated that the end portions 442 may have the cylindrical configuration, as illustrated fix example in FIGS. 6A-B.

The leg members 441 may have first bends 448 at their proximal ends that bend distally to join with angled leg members 443. The angled leg members 443 may extend from the first bends 448 to second bends 449 that bend proximally and attach to a central portion 451. The bends 448, 449 may provide the stabilizing member 440 a generally "M" shaped configuration. The bends 448, 449 may be living hinges that facilitate compression of the stabilizing members 440 as the first and second jaw members 402, 404 close the surgical clip 200. The stabilizing member 440 may be received into the first and/or second channels 408, 412 as the first and second jaw members 302, 304 approximate and/or close. The flexibility of the stabilizing members 440 may allow the surgical clip 200 to lengthen as it closes and prevent the stabilizing members 440 from impeding the closure of the first and second jaw members 402, 404.

The central portion 451 may be configured to receive and stabilize the proximal portion (e.g., the hinge member 206)

of the surgical clip 200. For example, the central portion 451 may have an aperture 450 configured to receive the proximal portion of the surgical clip 200 and reduce lateral movement of the surgical clip 200. The central portion 451 may, additionally or alternatively, have longitudinal walls 446 forming a cavity therein configured to receive the proximal portion of the surgical clip 200. The longitudinal walls 446 may extend proximally from the central portion 451 of the stabilizing member 440 toward the hinge member 406. In that sense, the longitudinal walls 446 may have a length and/or width greater than the immediately proximate portions of the stabilizing member 440. The longitudinal walls 446 may extend along the proximal portion of the surgical clip 200 to increase stability.

Figure 4:
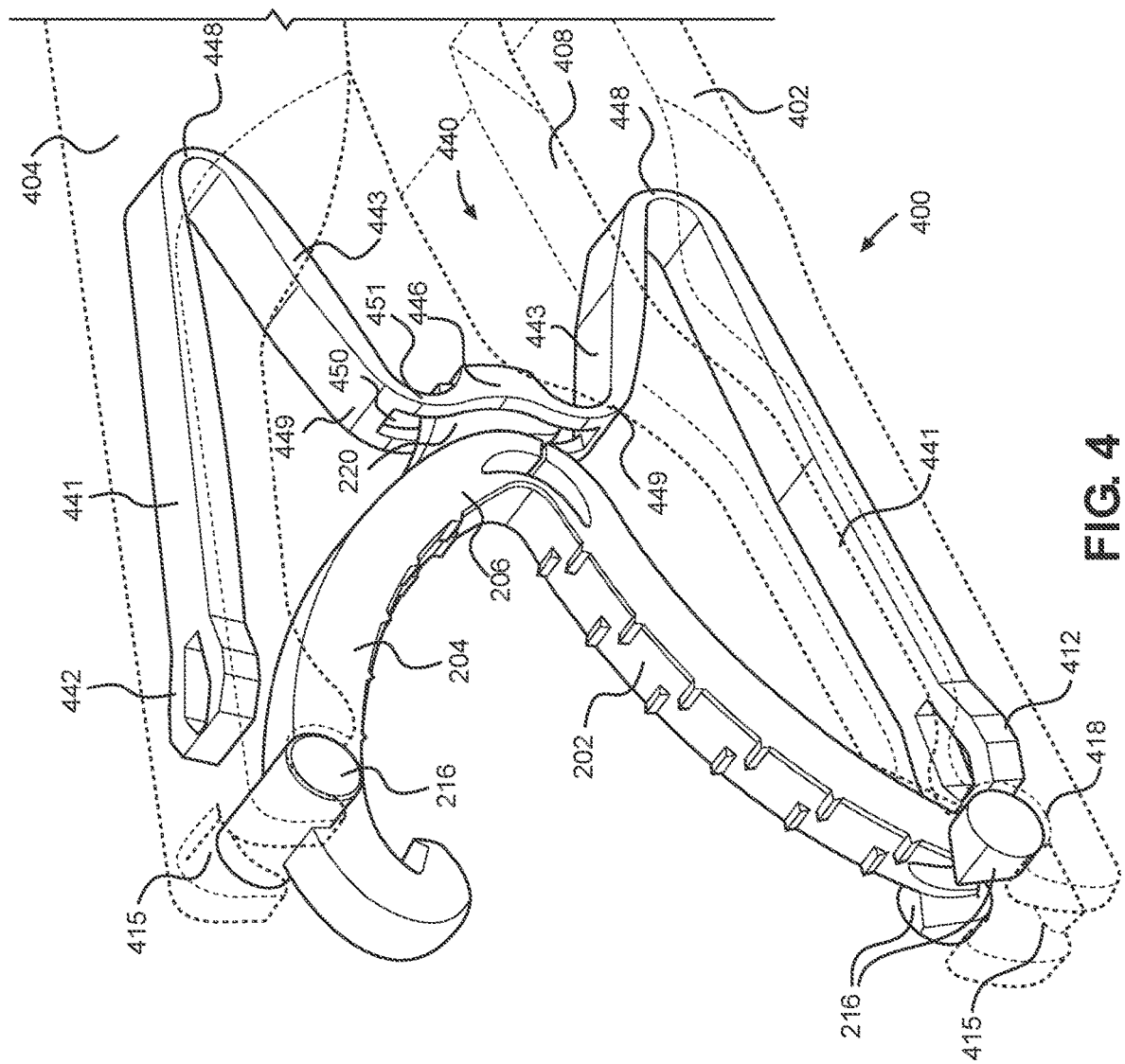
FIG. 4 illustrates an exemplary embodiment of an exemplary surgical clip loaded in the exemplary clip applier having the exemplary stabilizing member of the third embodiment of FIGS. 3A-C.

FIG. 4 illustrates a second embodiment of the surgical clip 200 loaded into the clip applier 400. As illustrated, the surgical clip 200 may include a tail or extension member 220 extending from the proximal portion of the surgical clip 200 configured to be received in the aperture 450 of the stabilizing member 400. The extension member 220 may extend proximally from a proximal portion e.g., the hinge portion 206) and have a hook portion that curves vertically. The extension may have a width less than a width of the hinge portions 206 and/or the leg members 202, 204. The extension member 220 may facilitate loading of the surgical clip 200 between the first and second jaw members 402, 404 and into the aperture 450, when the surgical clip 200 is in either orientation. Although FIG. 4 illustrates the second embodiment of the surgical clip 200 being loaded into the clip applier 400, the second embodiment of the surgical clip 200 may be loaded into any number of other clip appliers, including the other embodiments of the present disclosure.

As illustrated in FIGS. 5A-B, the clip applier 400 may be assembled by receiving the stabilizing members 440 and/or the surgical clip 200 from a cartridge 500. The cartridge 500 may include a first compartment 502 containing a stabilizing member 440 and/or one or more second compartments 504 containing at least one surgical clip 200. For example, the cartridge 500 may include a single first compartment 502 and a plurality of second compartments 504 aligned along a longitudinal axis of the cartridge 500. The number of second compartments 504 may be based on the applicable surgical procedure.

As further illustrated in FIGS. 5A-B, the clip applier 400 may be assembled according to a method including inserting the first and second jaw members 402, 404 into the first compartment 502. The stabilizing member 440 may be secured to the first and second jaw members 402, 404 by receiving the stabilizing member 440 into the open distal ends 415 of the longitudinal channels 408, 412. The method may further include inserting the jaw members 402, 404 into the second compartment 404 to secure the surgical clip 200 to the jaw members 402, 404 and the stabilizing member 440. For example, the jaw members 402, 404 may receive a boss 216 of the surgical clip 200 in the recesses 418, and the hinge member 206 of the surgical clip 200 may be engaged by the stabilizing member 440. The clip applier 400 may be configured to compress and/or latch the loaded surgical clip 200 onto tissue. The clip applier 400 may then be loaded with a second surgical clip 200 using the same stabilizing member 440 for the second surgical clip 200 to be applied during the same procedure, for example on the same tissue. The stabilizing member 440 may be removed from the clip applier 400 and/or disposed of following the procedure.

FIG. 6A illustrates a clip applier 600 having a stabilizing member 640 and loaded with a surgical clip 200 in an open configuration, and FIG. 6B illustrates the stabilizing member 640. As illustrated, the clip applier 600 may have a first jaw member 602 and a second jaw member 604 pivotably coupled at a hinge member (not shown). The first and second jaw members 602, 604 may be configured to compress the surgical clip 200 onto tissue, for example, to ligate a blood vessel.

As further illustrated, the first and second jaw members 602, 604 may include at least one recess 618 at a distal portion and the stabilizing member 640 proximal of the at least one recess 618. A first longitudinal channel 608 may extend through an inner portion of the first jaw member 602, separating the first jaw member 602 into a pair of first extensions (not labeled). A second longitudinal channel 612 may extend through an inner portion of the second jaw member 604, separating the second jaw member 604 into a pair of second extensions (not labeled). Each of the extensions may have a recess 618 configured to receive opposing boss members 216, and each of the longitudinal channels 608, 612 may be configured to receive a portion of the surgical clip 200. Each of the first and second jaw members 602, 604 may have an open distal end 615 into the longitudinal channels 608, 612 to receive the stabilizing member 640.

The stabilizing member 640 may have leg members 641 with end portions 642 releasably securable to the first and second jaw members 602, 604 of the respective longitudinal channel 608, 612. The end portions 642 may be enlarged cylindrical members extending perpendicularly of the leg members 641. For assembly, the end portions 642 may pass through the open distal ends 615 of the first and second jaw members 602, 604 and snap into a recess of the longitudinal channel 608, 612 to releasably secure the stabilizing member 640 in the first and second jaw members 602, 604. After use, the stabilizing member 640 may be removed, for example, by pulling the stabilizing member 640 distally out of the first and second jaw members 602, 604. However, it is also contemplated that the end portions 442 may have the split leg configuration, as illustrated for example in FIGS. 3A-C.

The leg members 641 may have a bend 648 at their proximal ends that bend distally to join with a central portion 651. The bends 648 may have an obtuse angle and be living hinges that facilitate compression of the stabilizing members 640 as the first and second jaw members 602, 604 close the surgical clip 200. For example, the stabilizing member 640 may be received into the first and/or second channels 608, 612 as the first and second jaw members 602, 604 approximate and/or close. The flexibility of the stabilizing members 640 may allow the surgical clip 200 to lengthen as it closes and prevent the stabilizing members 640 from impeding the closure of the first and second jaw members 602, 604.

The central portion 651 may be configured to receive and stabilize the proximal portion (e.g., the hinge member 206) of the surgical clip 200. For example, the central portion 651 may have an aperture 650 configured to receive the proximal portion of the surgical clip 200 and reduce lateral movement of the surgical clip 200. The central portion 651 may, additionally or alternatively, have walls 646 forming a cavity therein configured to receive the proximal portion of the surgical clip 200. The walls 646 may extend laterally from the central portion 651 of the stabilizing member 640.

FIG. 7A illustrates a clip applier 700 having a stabilizing member 740 and loaded with a surgical clip 200 in an open configuration, and FIG. 7B illustrates the stabilizing member 740. As illustrated, the clip applier 700 may have a first jaw member 702 and a second jaw member 704 pivotably coupled at a hinge member (not shown). The first and second jaw members 702, 704 may be configured to compress the surgical clip 200 onto tissue, for example, to ligate a blood vessel.

As further illustrated, the first and second jaw members 702, 704 may include at least one recess 718 at a distal portion and the stabilizing member 740 proximal of the at least one recess 718. A first longitudinal channel 708 may extend through an inner portion of the first jaw member 702, separating the first jaw member 702 into a pair of first extensions (not labeled). A second longitudinal channel 712 may extend through an inner portion of the second jaw member 704, separating the second jaw member 704 into a pair of second extensions (not labeled). Each of the extensions may have a recess 718 configured to receive opposing boss members 216, and each of the longitudinal channels 708, 712 may be configured to receive a portion of the surgical clip 200. Each of the first and second jaw members 702, 704 may have an open distal end 715 into the longitudinal channels 708, 712 to receive the stabilizing member 740.

The stabilizing member 740 may have leg members 741 with end portions 742 releasably securable to the first and second jaw members 702, 704 inside of the respective longitudinal channel 708, 712. The end portions 742 may be enlarged cylindrical members extending perpendicularly of the leg members 741. For assembly, the end portions 742 may be received into the open ends 715 and snap into a recess of the longitudinal channel 708, 712 to releasably secure the stabilizing member 740 in the first and second jaw members 702, 704. After use, the stabilizing member 740 may be removed, for example, by pulling the stabilizing member 740 distally out of the first and second jaw members 702, 704. However, it is also contemplated that the end portions 742 may have the split leg configuration, as illustrated for example in FIGS. 3A-C.

The leg members 741 may have a bend 748 along their lengths and be joined by a central portion 751 having a central pivot bend 749. The bend 748 may substantially match the curvature of the second leg member 204. The bends 748, 749 may facilitate compression of the stabilizing members 740 as the first and second jaw members 702, 704 close the surgical clip 200. For example, the stabilizing member 740 may be received into the first and/or second channels 608, 612 as the first and second jaw members 602, 604 approximate and/or close. The flexibility of the stabilizing members 740 may allow the surgical clip 200 to lengthen as it closes and prevent the stabilizing members 740 from impeding the closure of the first and second jaw members 702, 704.

The central portion 751 may be configured to receive and stabilize the proximal portion (e.g., the hinge member 206) of the surgical clip 200. For example, the central portion 751 may have a plurality of walls 746 forming a cavity therein configured to receive the proximal portion of the surgical clip 200. As illustrated in FIG. 7B, the central portion 751 may have first and second walls 746 positioned on both sides of an aperture 750. The walls 746 may engage the proximal portion of the surgical clip 200 when the first and second jaw members 702, 704 are in an open configuration, while the proximal portion of the surgical clip 200 is not received within the aperture 750. However, the aperture 750 may be configured to receive the proximal portion of the surgical clip 200 during, if needed. The walls 746 may extend longitudinally from the central portion 751 of the stabilizing member 740 distally.

FIG. 8A illustrates a clip applier 800 having a stabilizing member 840 and loaded with a surgical clip 200 in an open configuration, and FIG. 8B illustrates the stabilizing member 840. As illustrated, the clip applier 800 may have a first jaw member 802 and a second jaw member 804 pivotably coupled at a hinge member (not shown). The first and second jaw members 802, 804 may be configured to compress the surgical clip 200 onto tissue, for example, to ligate a blood vessel.

As further illustrated, the first and second jaw members 802, 804 may include at least one recess 818 at a distal portion and the stabilizing member 840 proximal of the at least one recess 818. A first longitudinal channel 808 may extend through an inner portion of the first jaw member 802, separating the first jaw member 802 into a pair of first extensions (not labeled). A second longitudinal channel 812 may extend through an inner portion of the second jaw member 804, separating the second jaw member 804 into a pair of second extensions (not labeled). Each of the extensions may have a recess 818 configured to receive opposing boss members 216, and each of the longitudinal channels 808, 812 may be configured to receive a portion of the surgical clip 200. Each of the first and second jaw members 802, 804 may have an open distal end 815 into the longitudinal channels 808, 812 to receive the stabilizing member 840.

The stabilizing member 840 may have leg members 841 with end portions 842 releasably securable to the first and second jaw members 802, 804 inside of the respective longitudinal channel 808, 812. The end portions 842 may be enlarged cylindrical members extending perpendicularly of the leg members 841. For assembly, the end portions 842 may pass through the open distal ends 815 of the first and second jaw members 802, 804 and snap into a recess of the longitudinal channel 808, 812 to releasably secure the stabilizing member 640 in the first and second jaw members 602, 604. After use, the stabilizing member 840 may be removed, for example, by pulling the stabilizing member 840 distally out of the first and second jaw members 802, 804. However, it is also contemplated that the end portions 842 may have the split leg configuration, as illustrated for example in FIGS. 3A-C.

The leg members 841 may have bends 848 connecting to the central portion 851, and the leg members 841 may extend proximally from the bends 848. The bends 848 may be greater than 90 degrees. The bends 848 may be living hinges that facilitate compression of the stabilizing members 840 as the first and second jaw members 802, 804 close the surgical clip 200. For example, the stabilizing member 840 may be received into the first and/or second channels 808, 812 as the first and second jaw members 302, 304 approximate and/or close. The flexibility of the stabilizing members 840 may allow the surgical clip 200 to lengthen as it closes and prevent the stabilizing members 840 from impeding the closure of the first and second jaw members 802, 804.

The central portion 851 may be configured to receive and stabilize the proximal portion (e.g., the hinge member 206) of the surgical clip 200. For example, the central portion 851 may have an aperture 850 configured to receive the proximal portion of the surgical clip 200 and reduce lateral movement of the surgical clip 200. The central portion 851 may, additionally or alternatively, have walls 846 forming a cavity therein configured to receive the proximal portion of the surgical clip 200. The walls 846 may extend laterally from the central portion 851 of the stabilizing member 840.

FIG. 9A-C illustrates a clip applier 900 having a stabilizing member 940 and loaded with a surgical clip 200 in an open configuration. As illustrated, the clip applier 900 may have a first jaw member 902 and a second jaw member 904 pivotably coupled at a hinge member (not shown). The first and second jaw members 902, 904 may be configured to compress the surgical clip 200 onto tissue, for example, to ligate a blood vessel.

As further illustrated, the first and second jaw members 902, 904 may include at least one recess 918 at a distal portion and the stabilizing member 940 proximal of the at least one recess 918. A first longitudinal channel 908 may extend through an inner portion of the first jaw member 902, separating the first jaw member 902 into a pair of first extensions 910. A second longitudinal channel 912 may extend through an inner portion of the second jaw member 904, separating the second jaw member 904 into a pair of second extensions 914. Each of the extensions 910, 914 may have a recess 918 configured to receive opposing boss members 216, and each of the longitudinal channels 908, 912 may be configured to receive a portion of the surgical clip 200. Each of the first and second jaw members 902, 904 may have an open distal end 915 into the longitudinal channels 908, 912 to receive the stabilizing member 940.

The stabilizing member 940 may be a spring element. The stabilizing element 940 may snap into the first and second jaw members 902, 904 and apply a distal force to the surgical clip 200 to retain the surgical clip 200 between the jaw members 1002, 1004. For example, each of the first and second jaw members 902, 904 may include an opening 905 configured to releasably receive end portions 942 of the stabilizing member 940. In that sense, the stabilizing member 940 may be inserted between the first and second members 902, 904 in a compressed configuration through the open ends 915 and released for the end portions 942 to snap into the openings 905. After use, the stabilizing member 940 may be configured to be released by pressing the ends 942 to urge the stabilizing member 940 out of the openings 905, in order to be removed and/or disposed of. The stabilizing member 940 may be in the form of a single flat wire element having flat surfaces that overlap the proximal portion of the surgical clip 200 to reduce lateral movement of the surgical clip 200. For example, the stabilizing member 1040 may have a substantially rectangular cross-section. The proximal portion of the surgical clip 200 may be received in one or more cavities or spaces formed between opposing lateral flat surfaces of the wire element. Bends 948 of the wire element may also allow the flexible element to compress as the clip applier 900 compresses. Additional bends 949 may fit the wire element around the proximal end portion of the surgical clip 200. The stabilizing member 940 may also have proximal support members 960 configured apply a distal force on the surgical clip 200 to help retain the bosses 212 in the recesses 918.

FIG. 10A-B illustrate a clip applier 1000 having a stabilizing member 1040 and loaded with a surgical clip 200 in an open configuration. As illustrated, the clip applier 1000 may have a first jaw member 1002 and a second jaw member 1004 pivotably coupled at a hinge member (not shown). The first and second jaw members 1002, 1004 may be configured to compress the surgical clip 200 onto tissue, for example, to ligate a blood vessel.

As further illustrated, the first and second jaw members 1002, 1004 may include at least one recess 1018 at a distal portion and the stabilizing member 1040 proximal of the at least one recess 1018. A first longitudinal channel 1008 may extend through an inner portion of the first jaw member 1002, separating the first jaw member 1002 into a pair of first extensions 1010. A second longitudinal channel 1012 may extend through an inner portion of the second jaw member 1004, separating the second jaw member 1004 into a pair of second extensions 1014. Each of the extensions 1010, 1014 may have a recess 1018 configured to receive opposing boss members 216, and each of the longitudinal channels 1008, 1012 may be configured to receive a portion of the surgical clip 200. Each of the first and second jaw members 1002, 1004 may have an open distal end 1015 into the longitudinal channels 1008., 1012 to receive the stabilizing member 1040.

The stabilizing member 1040 may be a spring element. The stabilizing element 1040 may snap into the first and second jaw members 1002, 1004 and apply a distal force to the surgical clip 200 to retain the surgical clip 200 between the jaw members 1002, 1004. For example, each of the first and second jaw members 1002, 1004 may include an opening 1005 configured to releasable receive end portions 1042 of the stabilizing member 1040. In that sense, the stabilizing member 1040 may be inserted into a distal open ends 1015 between the first and second members 1002, 1004 in a compressed configuration and released for the end portions 1042 to expand and snap into the openings 1005. After use, the stabilizing member 1040 may be released by pressing the ends 1042 to urge the stabilizing member 1040 out of the openings 1005, and be removed and/or disposed of. The stabilizing member 1040 may be in the form of one or more flat wire element having a flat shape configured to overlap the proximal portion of the surgical clip 200 to reduce lateral movement of the surgical clip 200. For example, the stabilizing member 1040 may have a substantially rectangular cross-section. The proximal portion of the surgical clip 200 may be received in one or more cavities or spaces formed between opposing flat portions of the wire element. Bends 1048 of the wire element may also allow the flexible element to compress as the clip applier 1000 compresses. The flat wire element may be welded at a proximal end. The stabilizing member 1040 may also have proximal support members 1060 configured apply a distal force on the surgical clip 200 to help retain the bosses 212 in the recesses 1018.

FIG. 11A-D illustrate a clip applier 1100 having a stabilizing member 1140 and loaded with a surgical clip 200 in an open configuration. As illustrated, the clip applier 1100 may have a first jaw member 1102 and a second jaw member 1104 pivotably coupled at a hinge member 1106. The first and second jaw members 1102, 1104 may be configured to compress the surgical clip 200 onto tissue, for example, to ligate a blood vessel.

As further illustrated, the first and second jaw members 1102, 1104 may include at least one recess 1118 at a distal portion and the stabilizing member 1140 proximal of the at least one recess 1118. A first longitudinal channel 1108 may extend through an inner portion of the first jaw member 1102, separating the first jaw member 1102 into a pair of first extensions 1110. A second longitudinal channel 1112 may extend through an inner portion of the second jaw member 1104, separating the second jaw member 1104 into a pair of second extensions (not labeled). Each of the extensions 1110 may have a recess 1118 configured to receive opposing boss members 216, and each of the longitudinal channels 1108, 1112 may be configured to receive a portion of the surgical clip 200. Each of the first and second jaw members 1102, 1104 may have an open distal end into the longitudinal channels 1108, 1112 to receive the stabilizing member 1140.

Figure 11B:
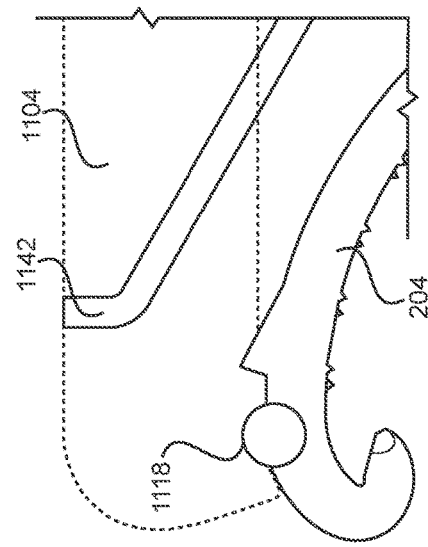
FIG. 11B illustrates an enlarged view of the exemplary clip applier having the exemplary stabilizing member and loaded with the exemplary surgical clip of the ninth exemplary embodiment of FIG. 11A.
Figure 11D:
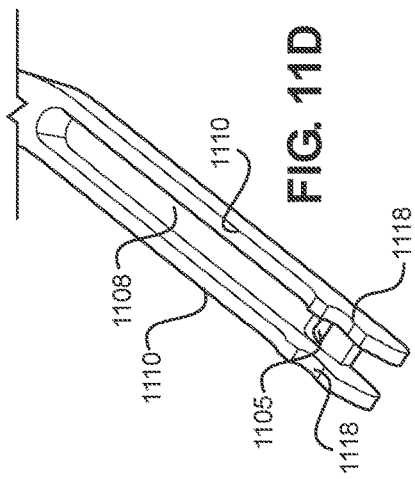
FIG. 11D illustrates an exploded view the exemplary clip applier of the ninth exemplary embodiment of FIG. 11A.
Figure 11A:
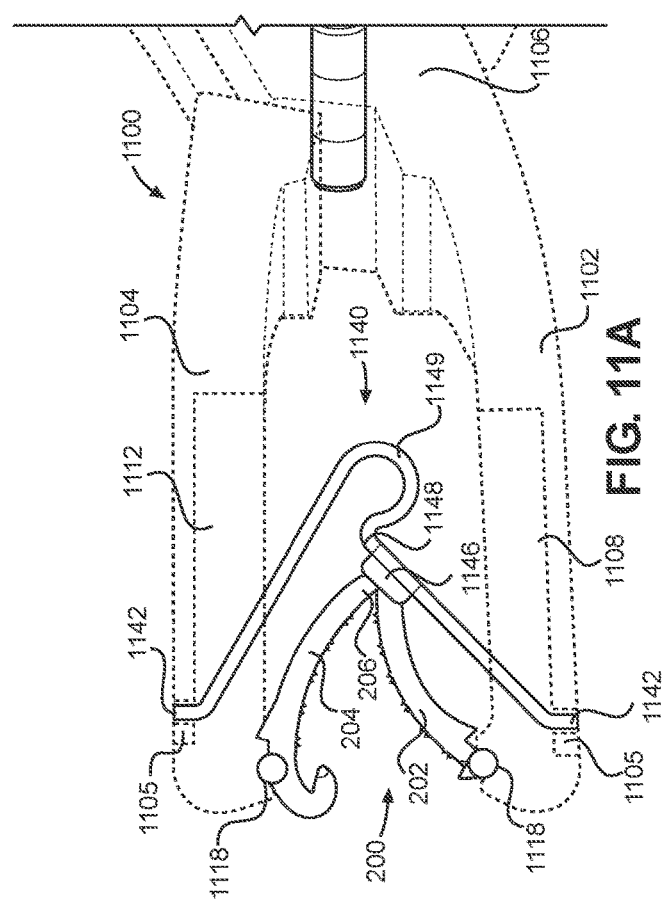
FIG. 11A illustrates a side view of a ninth exemplary embodiment of an exemplary clip applier having an exemplary stabilizing member and loaded with an exemplary surgical clip.
Figure 11C:
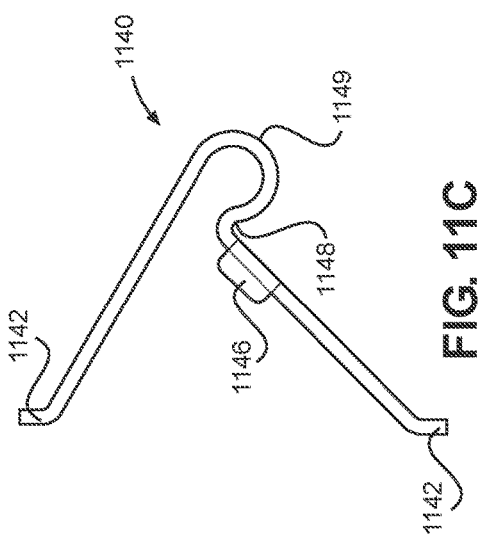
FIG. 11C illustrates a side view of the exemplary stabilizing member of the ninth exemplary embodiment of FIG. 11A.
Figure 12B:
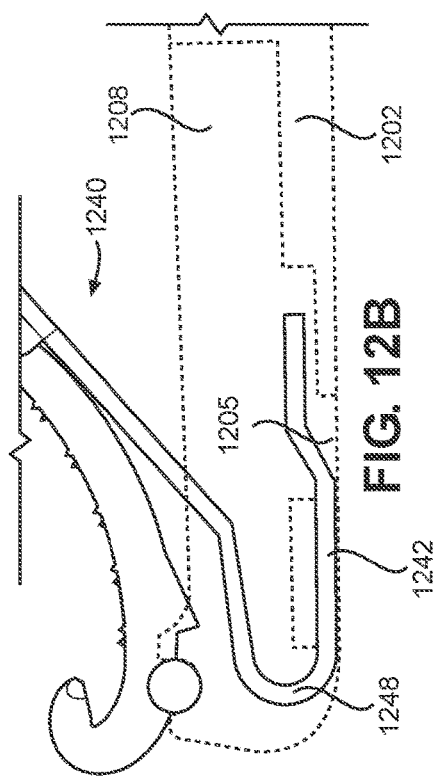
FIG. 12B illustrates an enlarged perspective view of the clip applier and the stabilizing member and loaded with the exemplary surgical clip of the tenth exemplary embodiment of FIG. 12A.
Figure 12D:
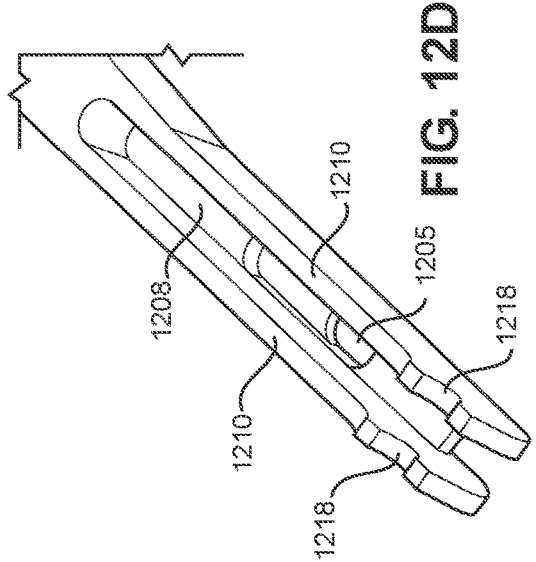
FIG. 12D illustrates an enlarged view of the exemplary clip applier of the tenth exemplary embodiment of FIGS. 12A-B.
Figure 12A:
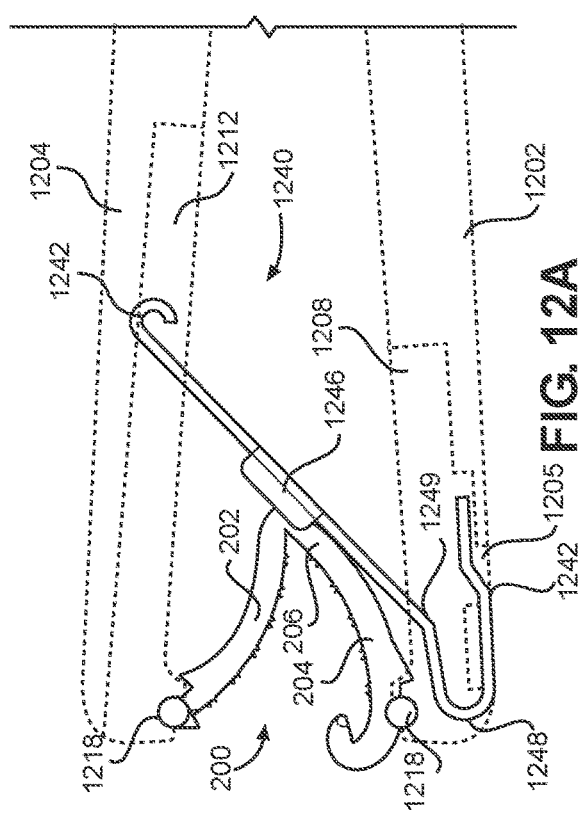
FIG. 12A illustrates a side view of a tenth exemplary embodiment of an exemplary clip applier having an exemplary stabilizing member and loaded with an exemplary surgical clip.
Figure 12C:
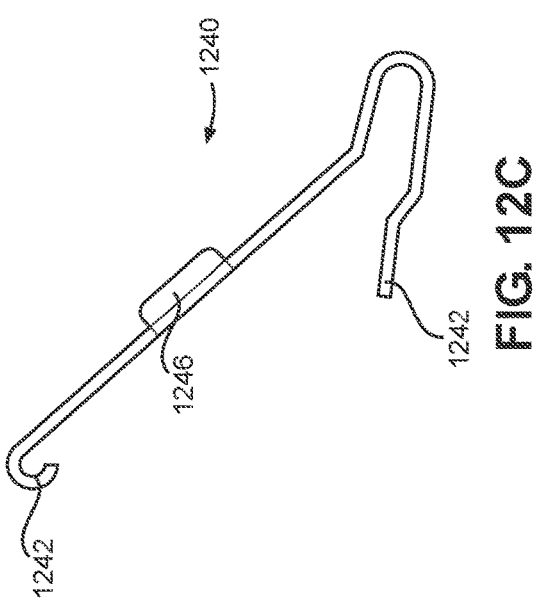
FIG. 12C illustrates a side view of the exemplary stabilizing member of the tenth exemplary embodiment of FIGS. 12A-B.

The stabilizing member 1140 may be a spring element. The stabilizing element 1140 may snap into the first and second jaw members 1102, 1104 and apply a distal force to the surgical clip 200 to retain the surgical clip 200 between the jaw members 1102, 1104. For example, each of the first and second jaw members 1102, 1104 may include an opening 1105 configured to releasably receive terminal end portions 1142 of the stabilizing member 1140. In that sense, the stabilizing member 1140 may be inserted into the open distal ends in a compressed configuration and released for the end portions 1142 to expand and snap into the openings 1005. After use, the stabilizing member 1140 may be released by pressing the ends 1142 to urge the stabilizing member 1140 out of the openings 1105, in order to be removed and/or disposed of. The stabilizing member 1140 may be in the form of a single wire element extending between the first and second jaw members 1102, 1104. The stabilizing member 1140 may include first and second longitudinal walls 1146 having a cavity configured to receive the proximal portion of the surgical clip 200 and to reduce lateral movement of the surgical clip 200. Bends 1148, 1149 of the flexible element may be living hinges to allow the flexible element to compress as the clip applier 1100 compresses. As illustrated in FIGS. 11A,D, the longitudinal channels 1108, 1112 may be sized to receive the wire element 1140 when the first and second jaw members 1102, 1104 are in a closed configuration.

FIG. 12A-D illustrate a clip applier 1200 having a stabilizing member 1240 and loaded with a surgical clip 200 in an open configuration. As illustrated, the clip applier 1200 may have a first jaw member 1202 and a second jaw member 1204 pivotably coupled at a hinge member (not shown). The first and second jaw members 1202, 1204 may be configured to compress the surgical clip 200 onto tissue, for example, to ligate a blood vessel.

As further illustrated, the first and second jaw members 1202, 1204 may include at least one recess 1218 at a distal portion and the stabilizing member 1240 proximal of the at least one recess 1218. A first longitudinal channel 1208 may extend through an inner portion of the first jaw member 1202, separating the first jaw member 1202 into a pair of first extensions 1210. A second longitudinal channel 1212 may extend through an inner portion of the second jaw member 1204, separating the second jaw member 1204 into a pair of second extensions (not labeled). Each of the extensions 1210 may have a recess 1218 configured to receive opposing boss members 216, and each of the longitudinal channels 1208, 1212 may be configured to receive a portion of the surgical clip 200. Each of the first and second jaw members 1202, 1204 may have an open distal end into the longitudinal channels 1208, 1212 to receive the stabilizing member 1240.

The stabilizing member 1240 may be a spring element that applies a distal force to the surgical clip 200 to retain the surgical clip 200 between the jaw members 1202, 1204. A first end portion 1242 of the stabilizing member 1240 may be releasably interlaced with an opening 1205 of the first jaw member 1202. As further illustrated, the first end portion 1242 may be wrapped around an open distal end of the first jaw member and received in the opening 1205 such that a terminal end of the end portion 1242 may be received in a recessed portion of the first longitudinal slot 1208. A second end portion 1242 may be slidably received in the second longitudinal channel 1212 and have a hooked end to reduce friction between the stabilizing member 1240 and the second jaw member 1204. After use, the stabilizing member 1240 may be released by pulling the first end portion 1242 out of the opening 1205, in order to be removed and/or disposed of. The stabilizing member 1240 may include first and second longitudinal walls 1246 having a cavity configured to receive the proximal portion of the surgical clip 200 and to reduce lateral movement of the surgical clip 200. Bends 1248, 1249 of the flexible element 1240 may allow the flexible element 1240 to compress as the clip applier 1200 compresses. The second portion 1242 may be configured to slide along the second jaw member 1204, and the first and/or second longitudinal channels 1208, 1212 may receive the stabilizing member 1240 in a closed configuration.

FIG. 13A-D illustrate a clip applier 1300 having a stabilizing member 1340 and loaded with a surgical clip 200 in an open configuration. As illustrated, the clip applier 1300 may have a first jaw member 1302 and a second jaw member 1304 pivotably coupled at a hinge member (not shown). The first and second jaw members 1302, 1304 may be configured to compress the surgical clip 200 onto tissue, for example, to ligate a blood vessel.

As further illustrated, the first and second jaw members 1302, 1304 may include at least one recess 1318 at a distal portion and the stabilizing member 1340 proximal of the at least one recess 1318. A first longitudinal channel 1308 may extend through an inner portion of the first jaw member 1302, separating the first jaw member 1302 into a pair of first extensions 1310. A second longitudinal channel 1312 may extend through an inner portion of the second jaw member 1304, separating the second jaw member 1304 into a pair of second extensions (not labeled). Each of the extensions 1310 may have a recess 1318 configured to receive opposing boss members 216, and each of the longitudinal channels 1308, 1312 may be configured to receive a portion of the surgical clip 200. Each of the first and second jaw members 1302, 1304 may have an open distal end into the longitudinal channels 1308, 1312 to receive the stabilizing member 1340.

The stabilizing member 1340 may be a spring element that applies a distal force to the surgical clip 200 to retain the surgical clip 200 between the jaw members 1302, 1304. A first end portion 1342 be slidably received in the second longitudinal channel 1308 and have a hooked end to reduce friction between the stabilizing member 1340 and the first jaw member 1304. A second end portion 1342 of the stabilizing member 1340 may be releasably secured into an opening 1305 of the second jaw member 1304, where the second end portion 1342 may slide longitudinally in the opening 1305. The stabilizing member 1340 may be inserted into the first and second jaw members 1302, 1304 by feeding the second end portion 1342 through the open distal end of the second leg member and into the opening 1305. The stabilizing member 1340 may then be rotating into place. After use, the stabilizing member 1340 may be released by pulling the first end portion 1342 out of the opening 1305, in order to be removed and/or disposed of. The stabilizing member 1340 may include first and second, longitudinal walls 1346 having a cavity configured to receive the proximal portion of the surgical clip 200 and to reduce lateral movement of the surgical clip 200. Bends 1348 of the flexible element 1240 allow the flexible element 1340 to compress as the clip applier 1300 compresses. The first end portion 1342 may be configured to slide along the second jaw member 1304, and the first and/or second longitudinal channels 1308, 1312 may receive the stabilizing member 1240 in a closed configuration.

FIG. 14A-B illustrate a clip applier 1400 having one or more stabilizing members 1440 and loaded with a surgical clip 200 in an open configuration. As illustrated, the clip applier 1400 may have a first jaw member 1402 and a second jaw member 1404 pivotably coupled at a hinge member (not shown). The first and second jaw members 1402, 1404 may be configured to compress the surgical clip 200 onto tissue, for example, to ligate a blood vessel.

As further illustrated, the first and second jaw members 1402, 1434 may include at least one engagement member 1416 at a distal portion and the one or more stabilizing members 1440 proximal of the at least engagement member 1416. A first longitudinal channel 1408 may extend through an inner portion of the first jaw member 1402, separating the first jaw member 1402 into a pair of first extensions (not labeled). A second longitudinal channel 1412 may extend through an inner portion of the second jaw member 1404, separating the second jaw member 1404 into a pair of second extensions (not labeled). The engagement members 1416 may be positioned in the longitudinal channels 1408, 1412, and each of the longitudinal channels 1408, 1412 may be configured to receive a portion of the surgical clip 200. The engagement members 1416 may be configured to engage the engagement members 214 as the surgical clip is pushed forward by the stabilizing member 1440. Each of the first and second jaw members 1402, 1404 may have an open distal end into the longitudinal channels 1408, 1412 to receive the stabilizing members 1440.

FIG. 14A illustrates an embodiment of the clip applier 1400 having a first stabilizing member 1440, and FIG. 14B illustrates an embodiment of the clip applier having first and second stabilizing members 1440. The stabilizing members 1440 may be spring elements that apply a distal force to the surgical clip 200 to retain the surgical clip 200 between the jaw members 1402, 1404. A first end portion 1442 for the first stabilizing member 1440 may be received in an opening 1405 of the first jaw member 1402, and a second end portion 1442 of the first stabilizing member 1440 may be pivotable received in the first jaw member. A first end portion 1442 for the second stabilizing member 1440 may be received in an opening 1405 of the second jaw member 1402, and a second end portion 1442 of the second stabilizing member 1440 may be pivotable received in the second jaw member. The flexible elements 1440 may be configured to compress as the clip applier 1400 compresses the surgical clip 200, and the flexible elements 1440 may be received in the first and/or second longitudinal channels 1408, 1412 in a dosed configuration. For example, in the embodiment of FIG. 14B, the first stabilizing member 1440 may be received in the first longitudinal channel 1408, and the second stabilizing member 1440 may be received in the second longitudinal channel 1412.

The various embodiments of the clip applier may therefore provide at least three-points of contact with the surgical clip. The clip applier may engage the distal portion of the surgical clip, and the clip applier may laterally align the surgical clip by receiving the proximal portion of the surgical dip in the cavity of the stabilizing member. The stabilizing member may pivot and/or compress as the surgical clip is compressed by the clip applier. The stabilizing member may also nest one or more longitudinal channels of jaw members of the surgical clip as the stabilizing member pivots and/or compresses.

The various embodiments of the surgical clip 200 of the present disclosure may be made of any suitable size and may be applied to any number of tissues, such as blood vessels, lymph nodes, nerves, fallopian tubes, or cardiac tissue. The surgical clip 200 may be constructed from any suitable biocompatible material, such as certain metals and polymers. However, the present invention is particularly suitable for practice with polymeric clips. Thus, the surgical clip 200 preferably has a one-piece integral polymeric body formed from a suitable strong biocompatible engineering plastic such as the type commonly used for surgical implants. Exemplary materials include homopolymer or co-polymer poly acetal, polyethylene terephthalate (PET), polybutylene terephthalate (PBT), polyoxymethylene, or other thermoplastic materials having similar properties that can be injection-molded, extruded or otherwise processed into like articles.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A clip applier configured to apply a surgical clip to tissue, the clip applier comprising:
    first and second jaw members configured to engage distal portions of the surgical clip, the first jaw member having a longitudinal channel in an inner portion extending along a longitudinal axis of the clip applier, and the first and second jaw members being configured to move relative to each other between an open configuration and a closed configuration; and
    a stabilizing member received in the longitudinal channel of the first jaw member and having an end portion secured to the first jaw member, the stabilizing member having an aperture and/or first and second walls configured to receive a proximal portion of the surgical clip to reduce lateral movement of the surgical clip,
    wherein the stabilizing member is flexible and configured to be compressed from a first configuration when the first and second jaw members are in the open configuration to a second configuration when the first and second jaw members are in the closed configuration.

2. The clip applier of claim 1, wherein the stabilizing member comprises the first and second walls, the first and second walls extend along the longitudinal axis of the clip applier and define a cavity therebetween configured to receive the proximal portion of the surgical clip.

3. The clip applier of claim 1, wherein the stabilizing member comprises the aperture configured to receive the proximal portion of the surgical clip and to reduce lateral movement of the surgical clip.

4. The clip applier of claim 1, wherein the stabilizing member comprises at least one bend that facilitates compression of the stabilizing member when the first and second jaw members close.

5. The clip applier of claim 1, wherein the longitudinal channel is configured to receive the stabilizing member when compressed.

6. The clip applier of claim 1, wherein the second jaw member has a channel in an inner portion that receives the stabilizing member, and the stabilizing member has a second end portion secured to the second jaw member.

7. The clip applier of claim 1, further comprising a second stabilizing member having an end portion secured to the second jaw member, wherein the second stabilizing member is configured to be compressed from a first configuration when the first and second jaw members are in the open configuration to a second configuration when the first and second jaw members are in the closed configuration.

8. The clip applier of claim 1, wherein the end portion of the stabilizing member is secured in the longitudinal channel of the first jaw member.

9. The clip applier of claim 1, wherein the end portion of the stabilizing member is releasably secured to the first jaw member.

10. The clip applier of claim 9, wherein the end portion of the stabilizing member comprises an enlarged end configured to snap into the first jaw member.

11. The clip applier of claim 1, wherein the stabilizing member comprises a spring element.

12. The clip applier of claim 1, wherein the stabilizing member comprises a plastic element.

13. A stabilizing member configured to be received between first and second jaw members of a clip applier and engage a proximal portion of a surgical clip, the stabilizing member comprising:
   a first portion having an enlarged end portion configured to be secured in a longitudinal channel in an inner portion of a first jaw member;
   a second portion having an enlarged end portion configured to be secured in a longitudinal channel in an inner portion of a second jaw member;
   a first bend and a second bend configured to facilitate compression of the stabilizing member when the first and second jaw members are in a closed configuration, the first bend positionable between a longitudinal axis of the clip applier and the first jaw member, and the second bend positionable between the longitudinal axis of the clip applier and the second jaw member; and
   an aperture and/or first and second walls between the first and second portions configured to receive a proximal portion of the surgical clip and to reduce lateral movement of the surgical clip.

14. The stabilizing member of claim 13, comprising the first and second walls, the first and second walls being longitudinal and defining a cavity configured to receive the proximal portion of the surgical clip.

15. The stabilizing member of claim 13, wherein the first bend is on a first side of the aperture and the second bend is on a second side of the aperture.

16. The stabilizing member of claim 13, wherein the stabilizing member comprises a spring element.

17. The stabilizing member of claim 13, wherein the stabilizing member comprises a plastic element.

18. A method of securing a surgical clip to a clip applier having first and second jaw members, the method comprising:
   securing a stabilizing member between the first and second jaw members by engaging a first end portion of the stabilizing member in a longitudinal channel in an inner portion of the first jaw member extending along a longitudinal axis of the clip applier and engaging a second end portion of the stabilizing member in a longitudinal channel in an inner portion of the second jaw member extending along the longitudinal axis of the clip applier;
   receiving the surgical clip between the first and second jaw members; and
   stabilizing the surgical clip with the stabilizing member to the clip applier by receiving a proximal portion of the surgical clip in an aperture and/or between first and second walls.

19. The method of claim 18, wherein stabilizing the surgical clip with the stabilizing member includes receiving the proximal portion of the surgical clip into the aperture of the stabilizing member.

20. The method of claim 18, further comprising:
   engaging a distal portion of a first leg member of the surgical clip with the first jaw member; and
   engaging a distal portion of a second leg member of the surgical clip with the second jaw member.

* * * * *